US007569542B2

(12) United States Patent
Eckert et al.

(10) Patent No.: US 7,569,542 B2
(45) Date of Patent: Aug. 4, 2009

(54) ANTI-MICROBIAL TARGETING CHIMERIC PHARMACEUTICAL

(75) Inventors: Randal Eckert, Los Angeles, CA (US); Fengxia Qi, Harbor City, CA (US); Wenyuan Shi, Los Angeles, CA (US); Maxwell H. Anderson, Seattle, WA (US)

(73) Assignee: The Regents of the University of California, Oakland, CA (US)

( * ) Notice: Subject to any disclaimer, the term of this patent is extended or adjusted under 35 U.S.C. 154(b) by 131 days.

(21) Appl. No.: 10/706,391

(22) Filed: Nov. 12, 2003

(65) Prior Publication Data

US 2004/0137482 A1 Jul. 15, 2004

Related U.S. Application Data

(63) Continuation-in-part of application No. 10/077,624, filed on Feb. 14, 2002, which is a continuation-in-part of application No. 09/910,358, filed on Jul. 19, 2001, now abandoned, which is a continuation-in-part of application No. 09/378,577, filed on Aug. 20, 1999, now abandoned.

(51) Int. Cl.
*A61K 38/16* (2006.01)
*A61K 38/00* (2006.01)
*C07K 4/04* (2006.01)

(52) U.S. Cl. .......................... 514/12; 514/13; 514/14; 530/300; 530/324; 530/326; 530/327

(58) Field of Classification Search ...................... None
See application file for complete search history.

(56) References Cited

U.S. PATENT DOCUMENTS

| | | | | |
|---|---|---|---|---|
| 4,671,958 | A | 6/1987 | Rodwell | 424/1.53 |
| 5,057,313 | A | 10/1991 | Shih et al. | 424/1.53 |
| 5,332,567 | A * | 7/1994 | Goldenberg | 424/1.49 |
| 5,645,835 | A | 7/1997 | Fell, Jr. et al. | 424/134.1 |
| 5,646,119 | A | 7/1997 | Oppenheim et al. | 514/12 |
| 5,672,351 | A | 9/1997 | Chikindas et al. | 424/401 |
| 5,726,293 | A | 3/1998 | Seed | 530/413 |
| 5,851,527 | A | 12/1998 | Hansen | 424/178.1 |
| 5,910,573 | A | 6/1999 | Pluckthun et al. | 530/387.3 |
| 5,981,726 | A | 11/1999 | Pastan | 536/23.53 |
| 6,183,744 | B1 | 2/2001 | Goldenberg | 424/141.1 |
| 6,197,299 | B1 | 3/2001 | Dohlsten et al. | 424/183.1 |
| 6,492,328 | B2 | 12/2002 | Lehrer et al. | |
| 2004/0052814 | A1 * | 3/2004 | Shi et al. | 424/190.1 |

FOREIGN PATENT DOCUMENTS

| | | |
|---|---|---|
| EP | WO 99/58141 | 11/1999 |
| EP | WO 02/22686 A2 | 3/2002 |
| WO | WO 94/09817 | 5/1994 |
| WO | WO 00/11037 | 3/2000 |
| WO | WO 02/15931 | 2/2002 |
| WO | WO 02/102975 | 12/2002 |

OTHER PUBLICATIONS

Helmerhorst, E.J. et al., "Synthetic histatin analogues with broad-spectrum antimicrobial activity," Biochem. J., vol. 326, 1997, pp. 39-45, XP002087342.
Tamamura, H. et al., "Synthesis of Protegrin-Related Peptides and Their Antibacterial and Anti-human Immunodeficiency Virus Activity," Chem. Pharm. Bull., vol. 43, No. 5, 1995, pp. 853-858, XP000892198.
Database Biosis Biosciences Information Service, Philiadlephia, PA, US 2001, XP007901737, Yashin, B. et al., "Susceptibility of *Chlamydia trachomatis serovars* L2, D, and E to G-10 novispirin."
Marshall, S.A. et al., Spectrum and Antimicrobial Activity of Alexomycin (PNU-82, 127), a Peptide Compound Projected for Use in Animal Health, Diagn. Microbiol. Infect. Dis., vol. 33, 1999, pp. 181-186, XP002924752.
Sue M. Travis, et al., Bactericidal Activity of Mammalian Cathelicidin-Derived Peptides, Infection and Immunity, vol. 68 No. 5:2748-2755, American Society for Microbiology, May 2000 (United States).
Jens-M. Schroder, Commentary: Epithelial Peptide Anti-Biotics, Biochemical Pharmacology, vol. 57, pp. 121-134, 1999, Elsevier Science.
Manuel L. Penichet et al., Antibody-Cytokine Fusion Proteins For the Therapy of Cancer, Journal of Immunological Methods, vol. 248:91-1001 (2000), Elsevier Science B.V.
Peng Li et al., An Antimicrobial Peptide Gene Found in the Male Reproductive System Of Rats, Science vol. 291-1783-1785.
Sherie L. Morrison et al., Chimeric Human Antibody Molecules: Mouse Antigen-Binding Domains with Human Constant Region Domains, Proceedings of the National Academy Of Sciences U.S.A. vol. 81:6851-6855 (1984).
Kenneth T. Miyasaki et al., β-Sheet Antibiotic Peptides As Potential Dental Therapeutics, International Journal of Antimicrobial Agents, vol. 9:269-280 (1988), Elsevier Science, B.V.
Andrea Giacometti et al., "Antimicrobial Activity Of Polycationic Peptides," vol. 20:1265-1273 (1999), Elsevier Science, Inc.
Kate Fortney et al., *Haemophilus ducreyi* Is Susceptible to Protegrin, Antimicrobia Agents and Chemotherapy, vol. 42:2690-2693 (1998).
Database Dialog No. BG195051081. Ncolas, P., "Peptide as Weapons Against Microorganisms in the Chemical Defense System of Vertebrates." Annual Review of Microbiology, vol. 49, pp. 277-304 (1995).
European Search Report for European Patent Application No. EP 02752402.4-2406, dated Sep. 9, 2005 (4 pages).

(Continued)

*Primary Examiner*—Robert A Zeman
(74) *Attorney, Agent, or Firm*—Townsend and Townsend and Crew LLP

(57) ABSTRACT

The present invention is based on the discovery of a composition that provides targeted anti-microbial effect. Specifically the composition contains a targeting moiety which recognizes a target microbial organism and an anti-microbial peptide moiety which has anti-microbial activity. In addition, the present invention provides methods of treating a microbial infection, e.g., on mucosal surfaces by using the compositions provided by the present invention.

17 Claims, 14 Drawing Sheets

OTHER PUBLICATIONS

International Search Report for PCT/US02/22695 mailed Jan. 2, 2003 (4 pages).
European Examination Report mailed on Feb. 21, 2007, for EP Application No. EP 02752402.4 filed on Jul. 17, 2002, 6 pages.
European Examination Report mailed on May 16, 2008, for EP Application No. 02752402.4 filed on Jul. 17, 2002, 7 pages.
Restriction Requirement mailed on Feb. 10, 2004, for U.S. Appl. No. 09/910,358, filed Jul. 19, 2001, 5 pages.
Notice of Abandonment and Interview Summary mailed on Sep. 17, 2004, for U.S. Appl. No. 09/910,358, filed Jul. 19, 2001, 3 pages.
Restriction Requirement mailed on Nov. 1, 2005, for U.S. Appl. No. 10/077,624, filed Feb. 14, 2002, 8 pages.
Office Action mailed on Jun. 6, 2006, for U.S. Appl. No. 10/077,624, filed Feb. 14, 2002, 11 pages.
Office Communication mailed on Mar. 20, 2007, for U.S. Appl. No. 10/077,624, filed Feb. 14, 2002, 3 pages.
Office Communication and Notice to Comply mailed on Oct. 31, 2007, for U.S. Appl. No. 10/077,624, filed Feb. 14, 2002, 17 pages.

* cited by examiner

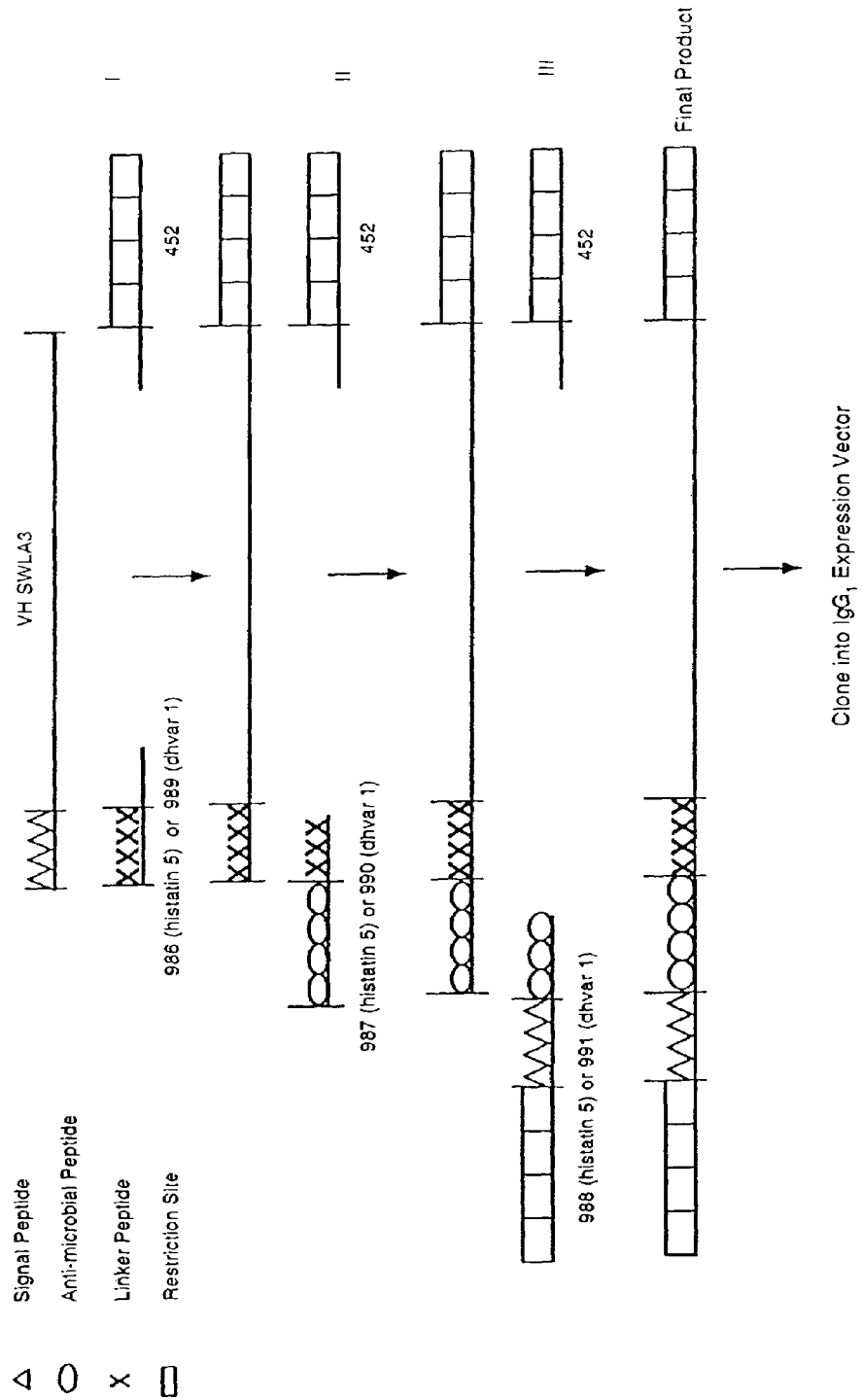

FIG. 2

Primers used in Sequential PCR Reactions:

986 (SEQ ID NO: 7) 5' CAC CAC TCG CAC AGA GGA TAC TCT GGT GGC GGT GGC TCG GGC GGA GGT GGG TCG GGT GGC GGC GGA TCC GAC GTG AAG CTT GTG GAG TC 3'

987 (SEQ ID NO: 8) 5' GGT GTC CAG TGT GAT AGC CAC GCT AAG CGG CAC CAC GGA TAT AAG CGG AAG TTC CAC GAG AAG CAC CAC TCG CAC AGA GGA TAC 3'

988 (SEQ ID NO: 9) 5' G GATATC CACC ATG GAC TTC GGG TTG AGC TTG GTT TTC CTT GTC CTT ACT TTA AAA GGT GTC CAG TGT GAT AGC C 3'

989 (SEQ ID NO: 10) 5' G TTC AGC CTG CGC AAG TAC TCT GGT GGC GGT GGC TCG GGC GGA GGT GGG TCG GGT GGC GGC GGA TCC GAC GTG AAG CTT GTG GAG TC 3'

990 (SEQ ID NO: 11) 5' GTC CTT ACT TTA AAA GGT GTC CAG TGT AAG CGG CTG TTT AAG GAG CTC AAG TTC AGC CTG CGC AAG TAC 3'

991 (SEQ ID NO: 12) 5' G GATATC CACC ATG GAC TTC GGG TTG AGC TTG GTT TTC CTT GTC CTT ACT TTA AAA GGT GTC CAG 3'

452 (SEQ ID NO: 13) 5' TGG GTC GAC WGA TGG GGS TGT TGT GCT AGC TGA GGA GAC 3'

FIG. 3

Histatin 5 Fusion to VH SWLA3: DNA and Amino Acid Sequence ggatatccac catggacttc gggttgagct tggtttcct tgtccttact ttaaaaggtg tccagtgt

| gat | agc | cac | gct | aag | cgg | cac | cac | gga | tat | aag | cgg | aag | ttc | cac | gag | aag | cac | cac | tcg |
|---|---|---|---|---|---|---|---|---|---|---|---|---|---|---|---|---|---|---|---|
| Asp | Ser | His | Ala | Lys | Arg | His | His | Gly | Tyr | Lys | Arg | Lys | Phe | His | Glu | Lys | His | His | Ser |

| cac | aga | gga | tac | tct | ggt | ggc | ggt | ggc | tcg | ggc | gga | ggt | ggg | tcg | ggt | ggc | ggc | gga | tcc |
|---|---|---|---|---|---|---|---|---|---|---|---|---|---|---|---|---|---|---|---|
| His | Arg | Gly | Tyr | <u>Ser</u> | <u>Gly</u> | <u>Gly</u> | <u>Gly</u> | <u>Gly</u> | <u>Ser</u> | <u>Gly</u> | <u>Gly</u> | <u>Gly</u> | <u>Gly</u> | <u>Ser</u> | <u>Gly</u> | <u>Gly</u> | <u>Gly</u> | <u>Gly</u> | <u>Ser</u> |

| gac | gtg | aag | ctt | gtg | gag | tct | ggg | gga | ggc | tta | gtg | aac | cct | gga | ggg | tcc | ctg | aaa | ctc |
|---|---|---|---|---|---|---|---|---|---|---|---|---|---|---|---|---|---|---|---|
| Asp | Val | Lys | Leu | Val | Glu | Ser | Gly | Gly | Gly | Leu | Val | Asn | Pro | Gly | Gly | Ser | Leu | Lys | Leu |

| tcc | tgt | gca | gcc | tct | gga | ttc | act | ttc | agt | agc | tat | acc | atg | tct | tgg | gtt | cgc | cag | act |
|---|---|---|---|---|---|---|---|---|---|---|---|---|---|---|---|---|---|---|---|
| Ser | Cys | Ala | Ala | Ser | Gly | Phe | Thr | Phe | Ser | Ser | Tyr | Thr | Met | Ser | Trp | Val | Arg | Gln | Thr |

| ccg | gag | aag | agg | ctg | gag | tgg | gtc | gca | tcc | att | agt | agt | ggt | ggt | act | tac | acc | tac | tat |
|---|---|---|---|---|---|---|---|---|---|---|---|---|---|---|---|---|---|---|---|
| Pro | Glu | Lys | Arg | Leu | Glu | Trp | Val | Ala | Ser | Ile | Ser | Ser | Gly | Gly | Thr | Tyr | Thr | Tyr | Tyr |

| cca | gac | agt | gtg | aag | ggc | cga | ttc | acc | atc | tcc | aga | gac | aat | gcc | aag | aac | acc | ctg | tac |
|---|---|---|---|---|---|---|---|---|---|---|---|---|---|---|---|---|---|---|---|
| Pro | Asp | Ser | Val | Lys | Gly | Arg | Phe | Thr | Ile | Ser | Arg | Asp | Asn | Ala | Lys | Asn | Thr | Leu | Tyr |

| ctg | caa | atg | acc | agt | ctg | aag | tct | gag | gac | aca | gcc | atg | tat | tac | tgt | tca | aga | gat | gac |
|---|---|---|---|---|---|---|---|---|---|---|---|---|---|---|---|---|---|---|---|
| Leu | Gln | Met | Thr | Ser | Leu | Lys | Ser | Glu | Asp | Thr | Ala | Met | Tyr | Tyr | Cys | Ser | Arg | Asp | Asp |

| ggc | tcc | tac | ggc | tcc | tat | tac | tat | gct | atg | gac | tac | tgg | ggt | caa | gga | acc | tca | gtc | acc |
|---|---|---|---|---|---|---|---|---|---|---|---|---|---|---|---|---|---|---|---|
| Gly | Ser | Tyr | Gly | Ser | Tyr | Tyr | Tyr | Ala | Met | Asp | Tyr | Trp | Gly | Gln | Gly | Thr | Ser | Val | Thr |

| gtc | tct | tca | gct | agc |
|---|---|---|---|---|
| Val | Ser | Ser | Ala | Ser |

FIG. 4

Dhvar 1 Fusion to VH SWLA3: DNA and Amino Acid Sequence ggatatccac catggacttc gggttgagct tggtttcct tgtccttact ttaaaaggtg tccagtgt

| aag | cgg | ctg | ttt | aag | gag | ctc | aag | ttc | agc | ctg | cgc | aag | tac | tct | ggt | ggc | ggt | ggc | tcg |
|---|---|---|---|---|---|---|---|---|---|---|---|---|---|---|---|---|---|---|---|
| Lys | Arg | Leu | Phe | Lys | Glu | Leu | Lys | Phe | Ser | Leu | Arg | Lys | Tyr | <u>Ser</u> | <u>Gly</u> | <u>Gly</u> | <u>Gly</u> | <u>Gly</u> | <u>Ser</u> |

| ggc | gga | ggt | ggg | tcg | ggt | ggc | ggc | gga | tcc | gac | gtg | aag | ctt | gtg | gag | tct | ggg | gga | ggc |
|---|---|---|---|---|---|---|---|---|---|---|---|---|---|---|---|---|---|---|---|
| <u>Gly</u> | <u>Gly</u> | <u>Gly</u> | <u>Gly</u> | <u>Ser</u> | <u>Gly</u> | <u>Gly</u> | <u>Gly</u> | <u>Gly</u> | <u>Ser</u> | Asp | Val | Lys | Leu | Val | Glu | Ser | Gly | Gly | Gly |

| tta | gtg | aac | cct | gga | ggg | tcc | ctg | aaa | ctc | tcc | tgt | gca | gcc | tct | gga | ttc | act | ttc | agt |
|---|---|---|---|---|---|---|---|---|---|---|---|---|---|---|---|---|---|---|---|
| Leu | Val | Asn | Pro | Gly | Gly | Ser | Leu | Lys | Leu | Ser | Cys | Ala | Ala | Ser | Gly | Phe | Thr | Phe | Ser |

| agc | tat | acc | atg | tct | tgg | gtt | cgc | cag | act | ccg | gag | aag | agg | ctg | gag | tgg | gtc | gca | tcc |
|---|---|---|---|---|---|---|---|---|---|---|---|---|---|---|---|---|---|---|---|
| Ser | Tyr | Thr | Met | Ser | Trp | Val | Arg | Gln | Thr | Pro | Glu | Lys | Arg | Leu | Glu | Trp | Val | Ala | Ser |

| att | agt | agt | ggt | ggt | act | tac | acc | tac | tat | cca | gac | agt | gtg | aag | ggc | cga | ttc | acc | atc |
|---|---|---|---|---|---|---|---|---|---|---|---|---|---|---|---|---|---|---|---|
| Ile | Ser | Ser | Gly | Gly | Thr | Tyr | Thr | Tyr | Tyr | Pro | Asp | Ser | Val | Lys | Gly | Arg | Phe | Thr | Ile |

| tcc | aga | gac | aat | gcc | aag | aac | acc | ctg | tac | ctg | caa | atg | acc | agt | ctg | aag | tct | gag | gac |
|---|---|---|---|---|---|---|---|---|---|---|---|---|---|---|---|---|---|---|---|
| Ser | Arg | Asp | Asn | Ala | Lys | Asn | Thr | Leu | Tyr | Leu | Gln | Met | Thr | Ser | Leu | Lys | Ser | Glu | Asp |

| aca | gcc | atg | tat | tac | tgt | tca | aga | gat | gac | ggc | tcc | tac | ggc | tcc | tat | tac | tat | gct | atg |
|---|---|---|---|---|---|---|---|---|---|---|---|---|---|---|---|---|---|---|---|
| Thr | Ala | Met | Tyr | Tyr | Cys | Ser | Arg | Asp | Asp | Gly | Ser | Tyr | Gly | Ser | Tyr | Tyr | Tyr | Ala | Met |

| gac | tac | tgg | ggt | caa | gga | acc | tca | gtc | acc | gtc | tct | tca | gct | agc |
|---|---|---|---|---|---|---|---|---|---|---|---|---|---|---|
| Asp | Tyr | Trp | Gly | Gln | Gly | Thr | Ser | Val | Thr | Val | Ser | Ser | Ala | Ser |

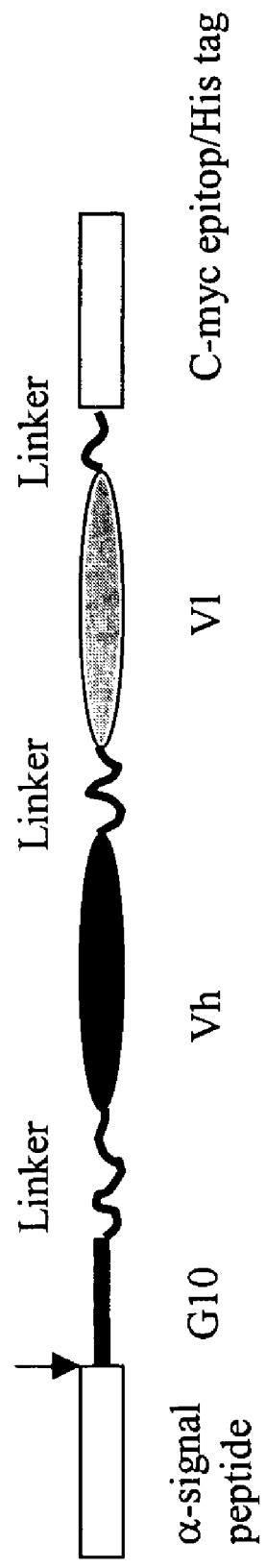
Fig. 5. Construction of PG-1-SWLA3 minibody fusion for expression in *Pichia* – final product

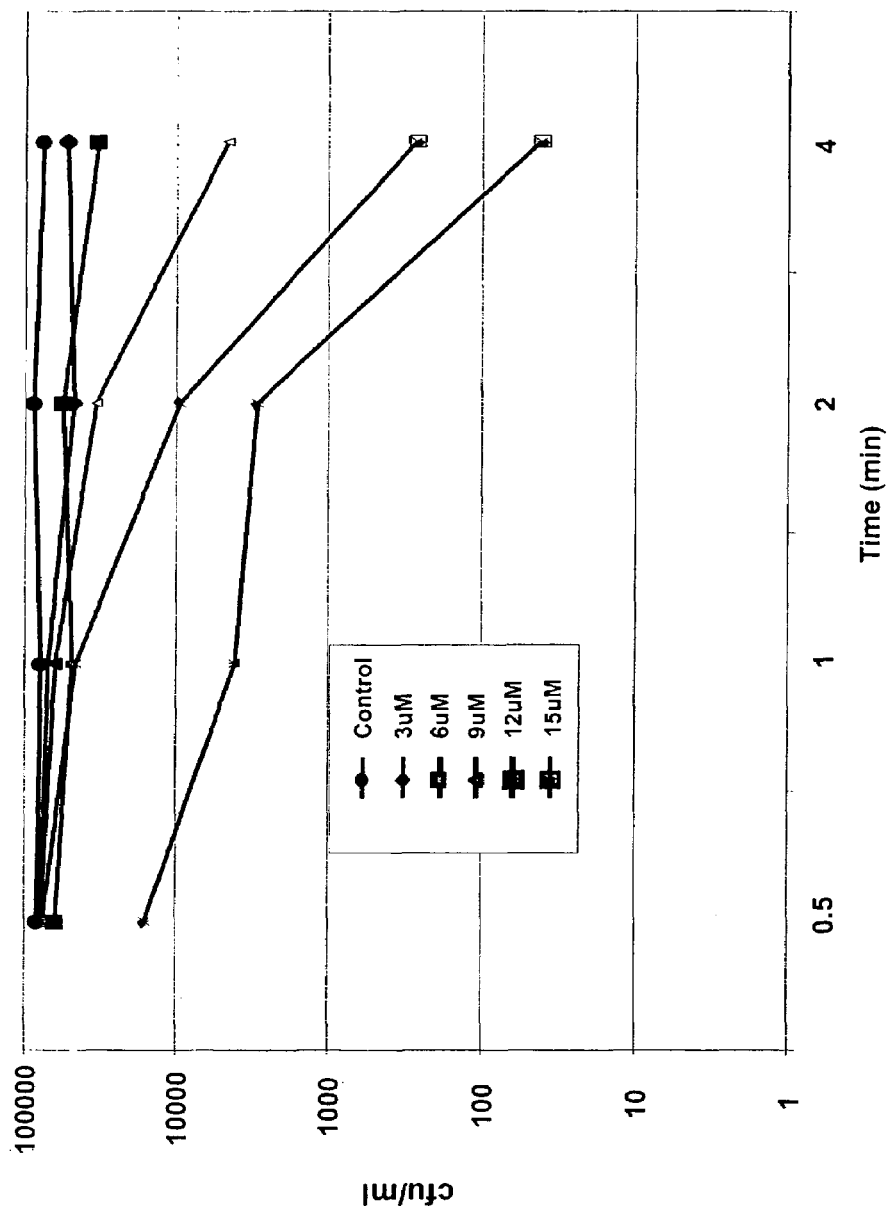

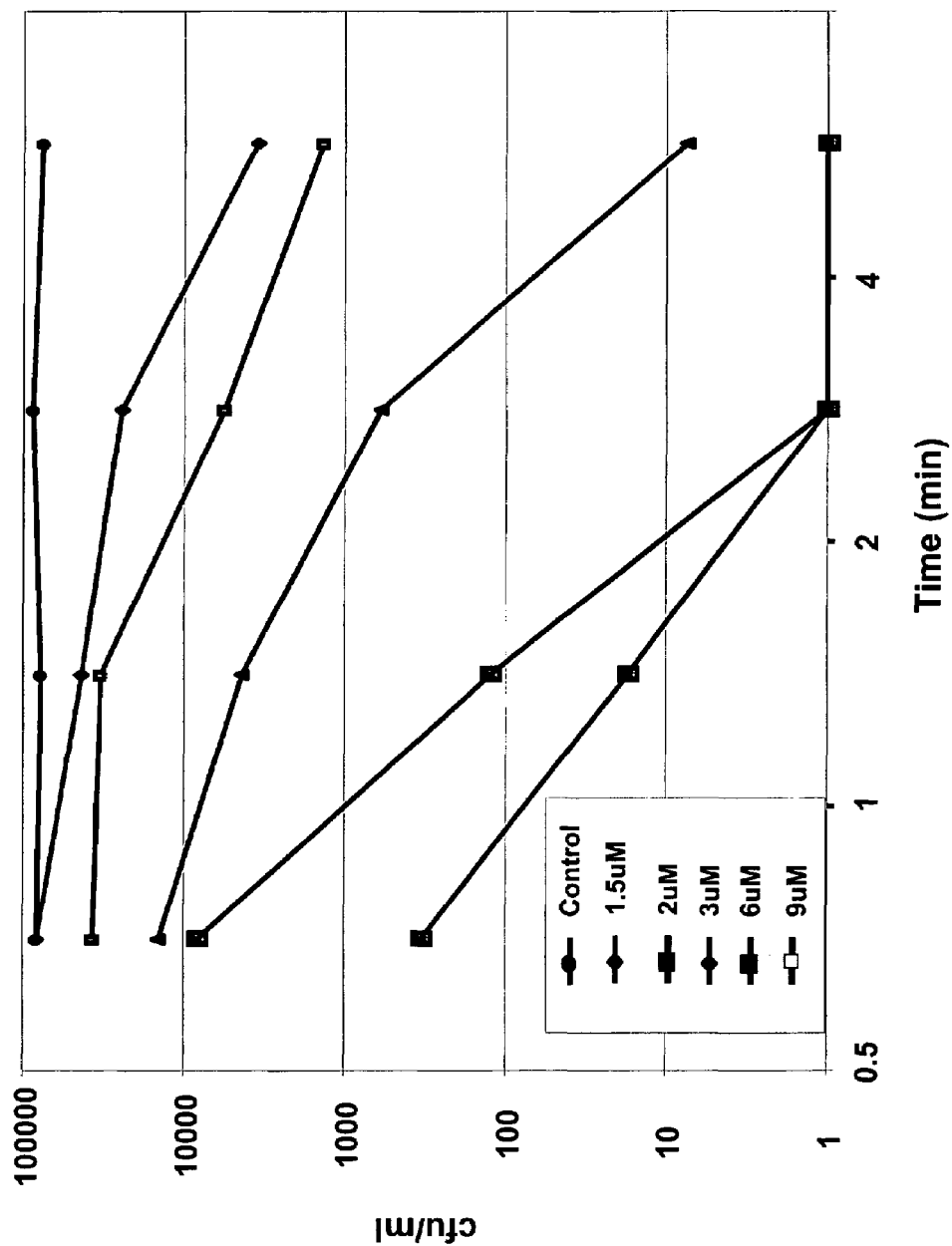

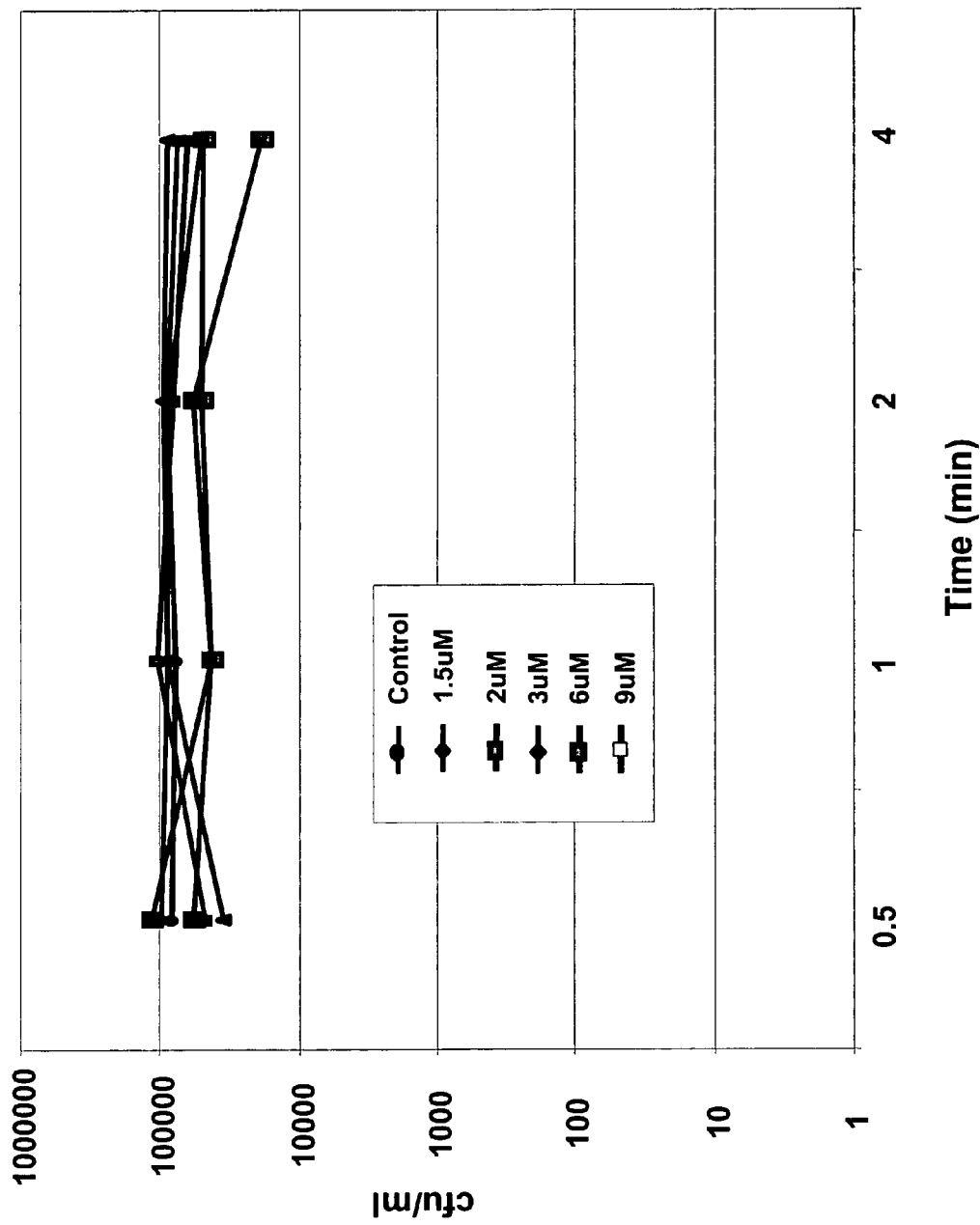
Figure 8. Time-Kill of G10CatN against *P. mendocina*

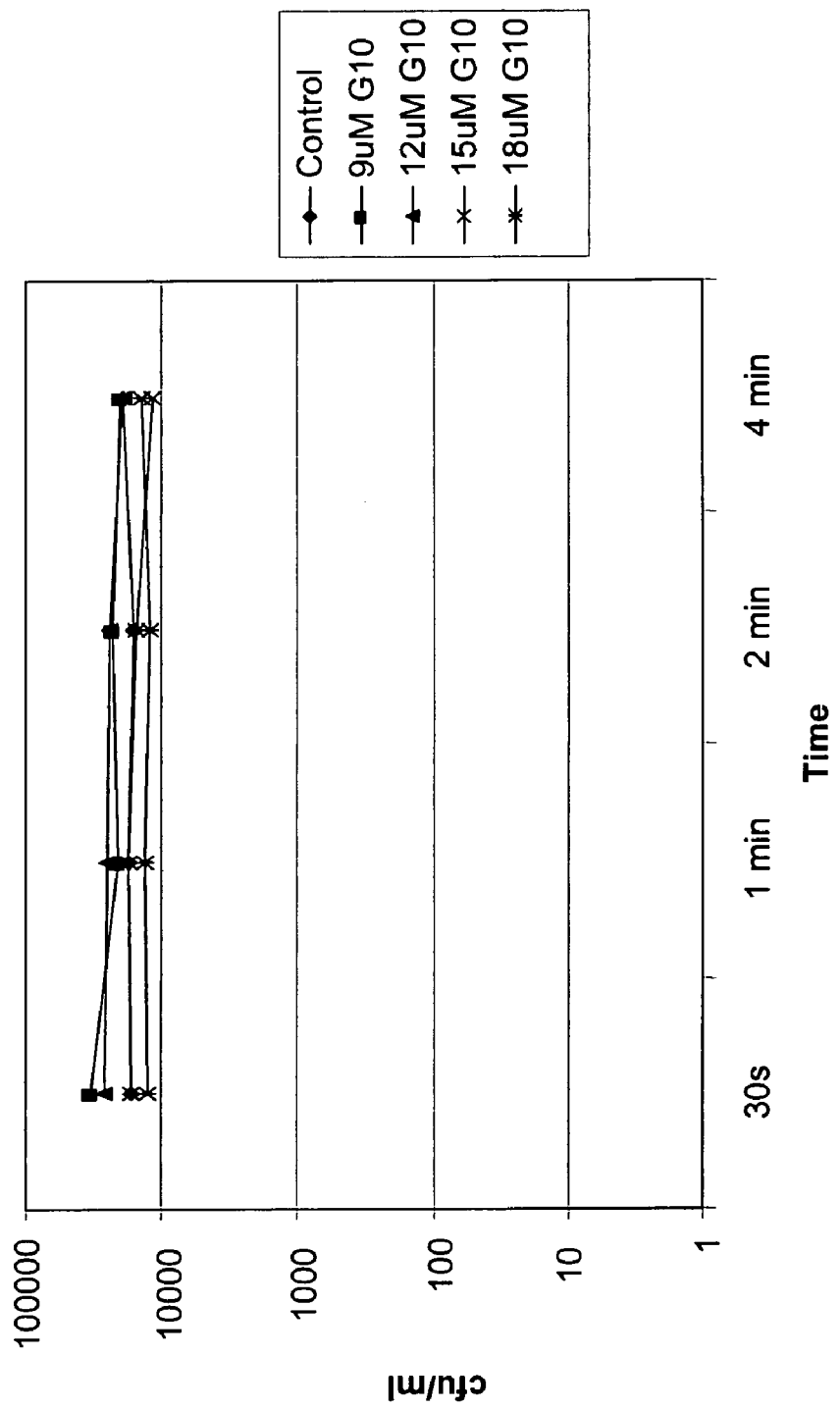
Fig. 9. Killing Kinetics of G10 against PAK

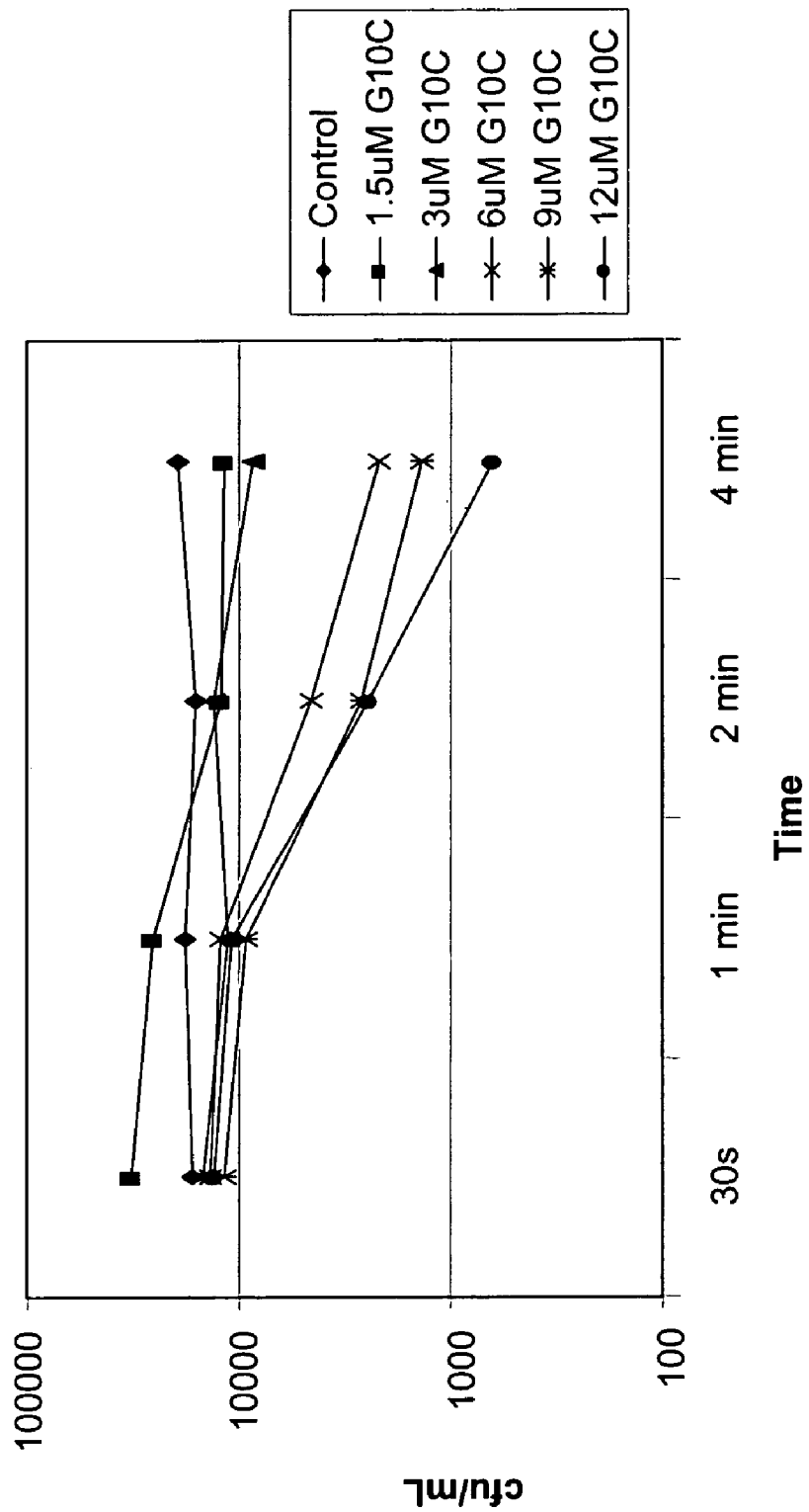
Fig. 10. Killing kinetics of G10CatC against PAK

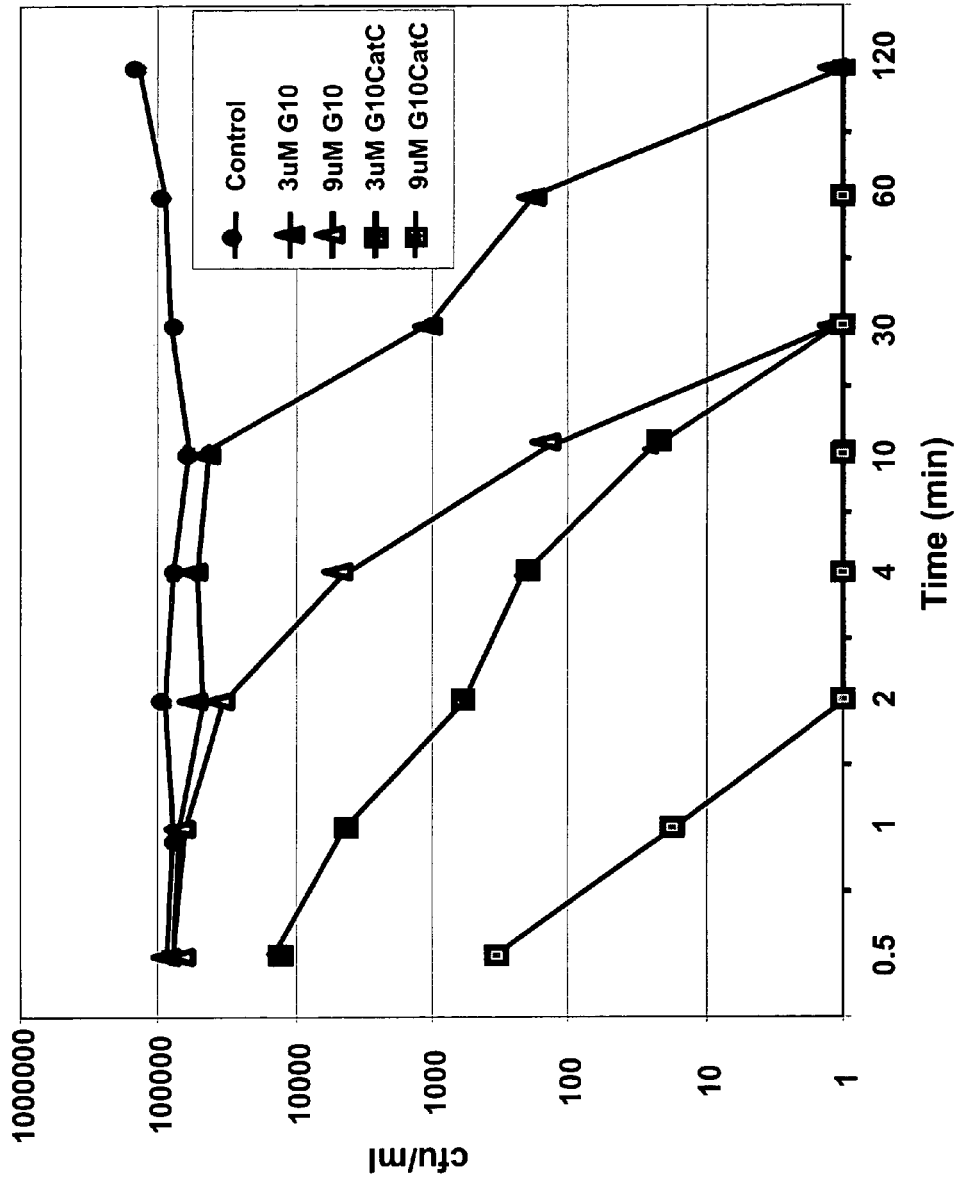
Figure 11. Time-Kill of G10 and G10CatC against *P. mendocina*

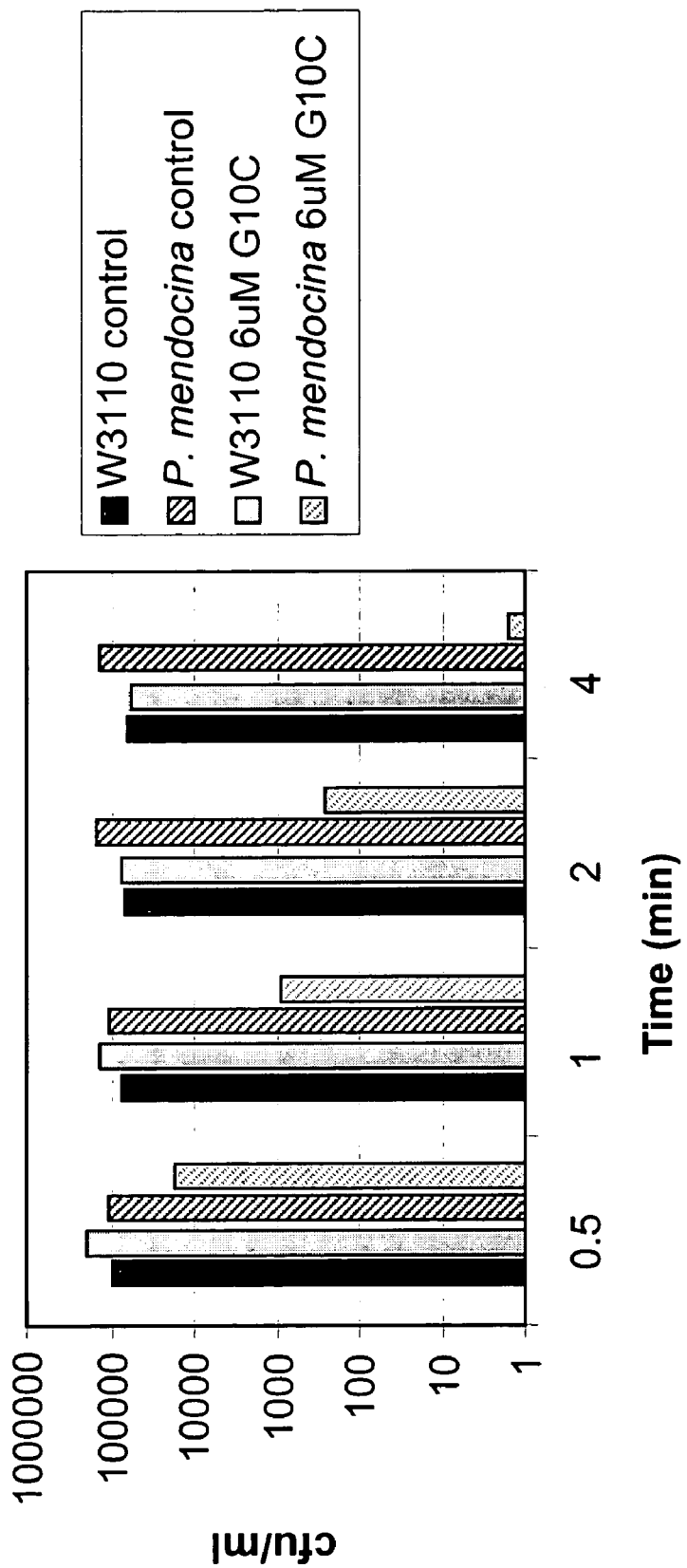
Figure 12. Selective killing of *P. mendocina* by G10CatC in mixed culture

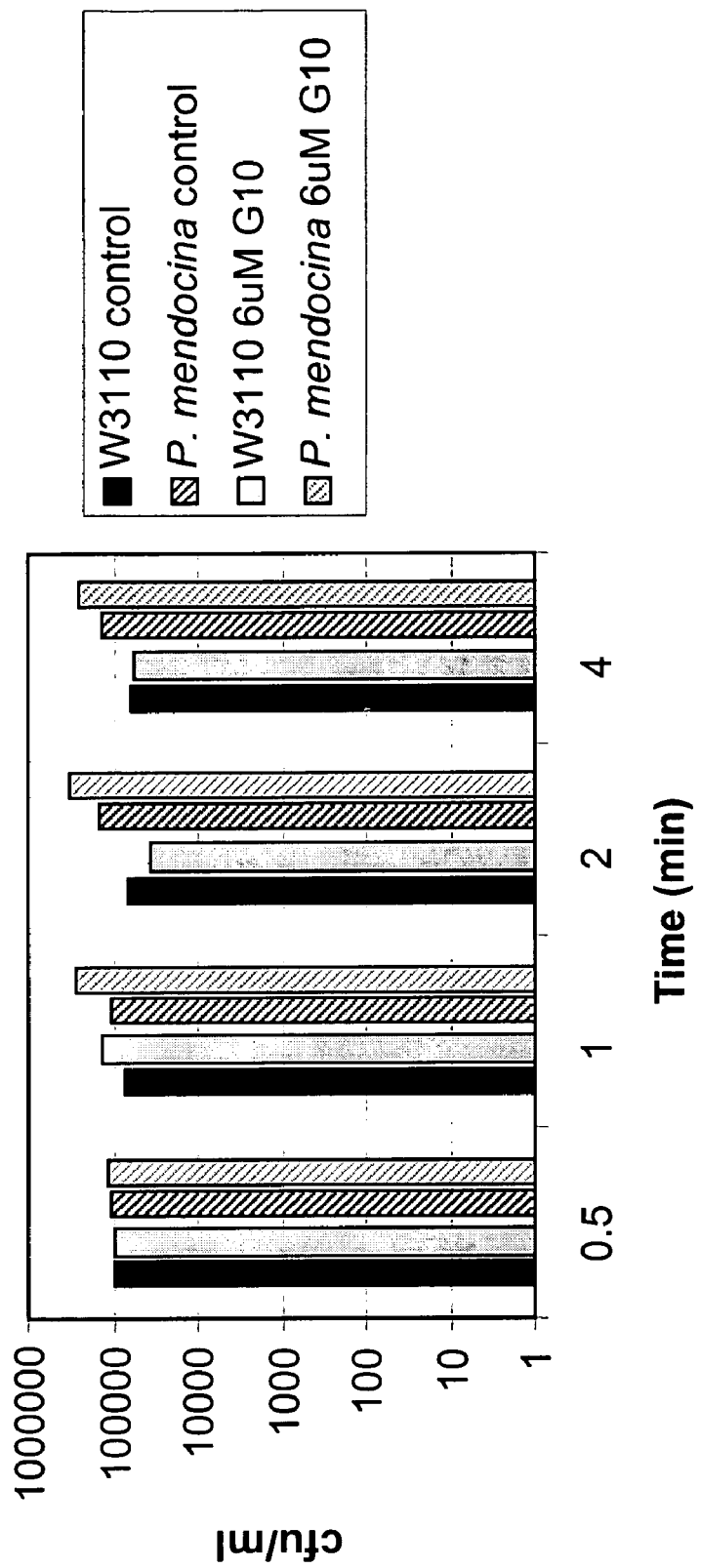
Figure 13. nonselective killing of *P. mendocina* by G10 in mixed culture

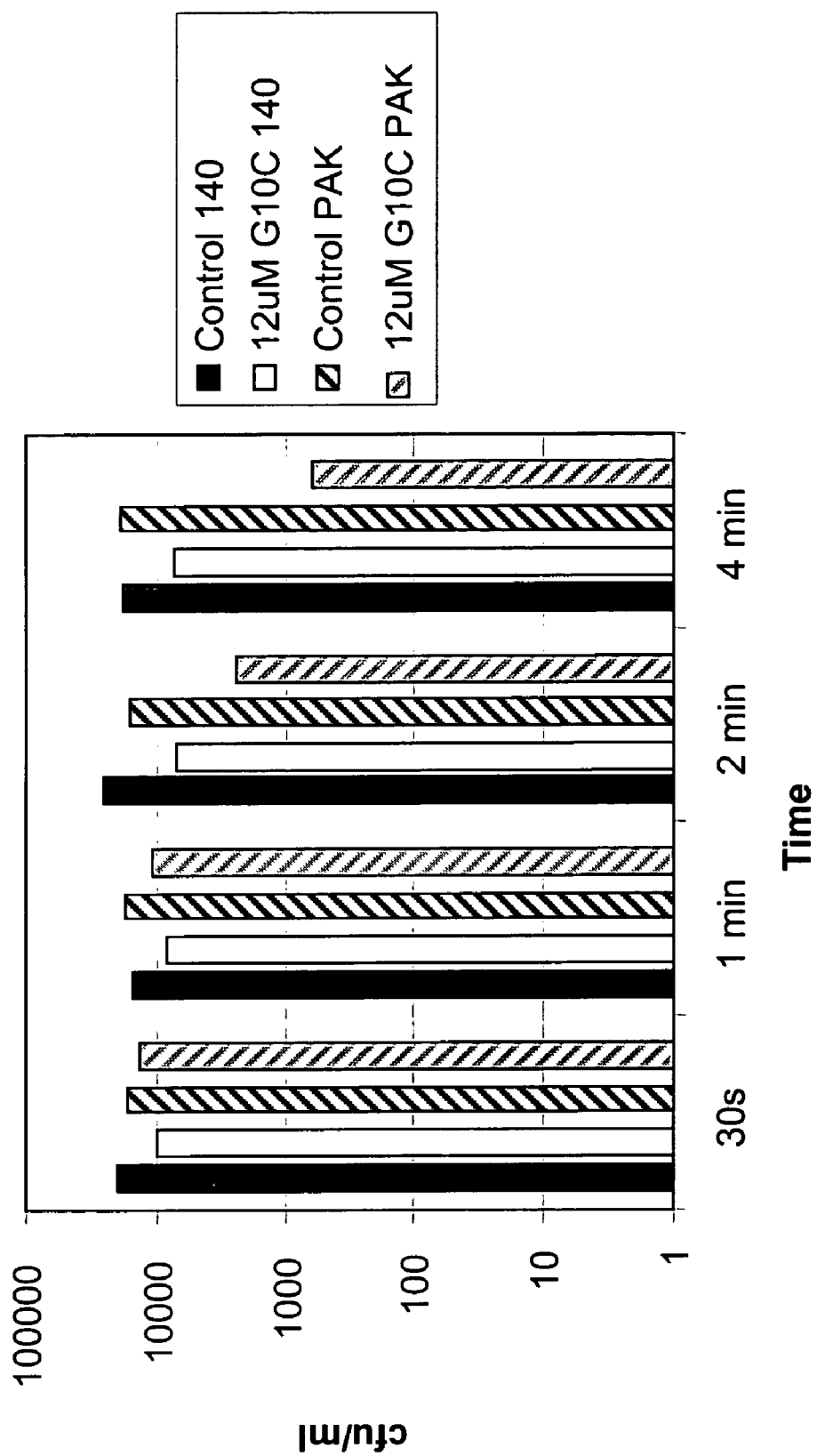
Fig. 14. Selective killing of PAK by G10C in mixed culture with *S. mutans*

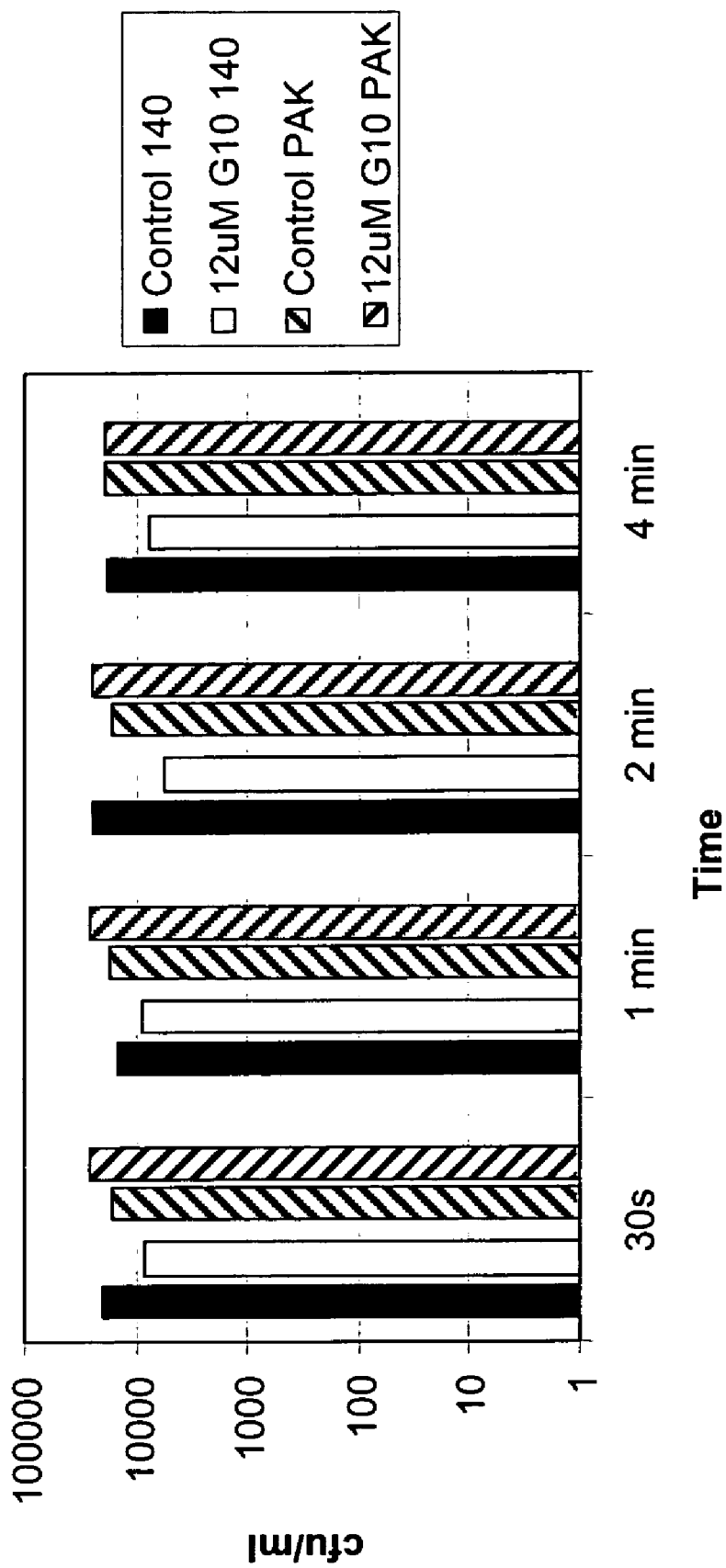
Fig. 15. No selective killing of PAK by G10 in mixed culture with *S. mutans*

ANTI-MICROBIAL TARGETING CHIMERIC PHARMACEUTICAL

CROSS REFERENCE TO RELATED APPLICATIONS

This application is a continuation-in-part of U.S. application Ser. No. 10/077,624, filed on Feb. 14, 2002 which is a continuation-in-part of U.S. application Ser. No. 09/910,358, filed on Jul. 19, 2001, now abandoned, which is a continuation-in-part of U.S. application Ser. No. 09/378,577, filed on Aug. 20, 1999, now abandoned, all of which are incorporated herein by reference.

FIELD OF THE INVENTION

This invention relates generally to the field of anti-microbial treatment and more specifically to targeted anti-microbial treatment by chimeric constructs.

BACKGROUND OF THE INVENTION

The Centers for Disease Control estimates that half of more than 100 million annual prescriptions of antibiotics are unnecessary. As a result, microbes have, in many cases, adapted and are resistant to antibiotics due to constant exposure and improper use of the drugs. It is estimated that the annual cost of treating drug resistant infections in the United States is approximately $5 billion. This continued emergence of anti-microbial-resistant bacteria, fungi, yeast and parasites has encouraged efforts to develop other agents capable of killing pathogenic microbes. Furthermore, there are urgent needs for target-specific anti-microbial agents since many microbial pathogens reside with non-harmful commensal bacteria that are important for the health of the human host.

Recent scientific studies have revealed a class of naturally occurring anti-microbial peptides in humans, other mammals, plants, insects and other organisms. A negative aspect of treatment with antibiotics or anti-microbial peptides is their indiscriminate killing or inhibition of a broad spectrum of microorganisms. The human body is home to millions of different bacteria, many of which are vital for optimal health. Overuse of broad-spectrum antibiotics can seriously disrupt the ecology of the normal human microbiota rendering humans more susceptible to bacterial, yeast, viral, and parasitic infections. This effect is also seen with administration of anti-microbial peptides. For example, the antibiotic peptide histatin kills most gram-positive bacteria in the oral cavity. Thus general administration of histatin can lead to undesirable effects by allowing the overgrowth of gram-negative bacteria, such as *Actinobacillus* sp or *Fusobacterium* sp, many of which may cause periodontal diseases. Accordingly, histatin is not useful by itself for prevention of dental caries.

Another disadvantage of administration of anti-microbial peptides is their ability to damage host cells at higher concentrations since these positively charged peptides can also penetrate and disrupt eukaryotic cell membranes.

Previous efforts to deliver of pharmaceutically active agents to specific targets relied principally on chemically conjugating a pharmaceutically active agent to a targeting component. For example Shih et al. U.S. Pat. No. 5,057,313 refers to targeting delivery of drugs, toxins and chelators to specific sites in an organism by loading a therapeutic or diagnostic component onto a polymeric carrier, followed by conjugation of the carrier to a targeting antibody. Hansen, U.S. Pat. No. 5,851,527 claims a similar invention.

A drawback to this approach is that the non-specific linkage of the pharmaceutical reagents to unknown sites on the antibody molecule used for targeting may interfere with delivery of the therapeutic agents. See Rodwell et al., U.S. Pat. No. 4,671,958. Moreover, chemical modification of a targeting antibody by the nonspecific reactions during conjugation may substantively alter the antibody itself, thereby affecting its binding to targets. Furthermore, chemical linkage is very inefficient and the result is non-uniform, making the technique very difficult to use in practice.

More recently, there have been a number of reports of the use of recombinant techniques to produce fusion proteins for the treatment of disease. See Penichet and Morrison, J. Immunological Methods, 248:91-101 (2001) for review. Penichet et al. discuss efforts to treat malignant disease using a genetically engineered protein construct including an immunological component that binds specifically to tumor cells and a cytokine capable of eliciting significant antitumor activity. See, e.g. Pastan et al. U.S. Pat. No. 5,981,726, and Fell, Jr. et al., U.S. Pat. No. 5,645,835.

However, to date there have not been any reports of directing anti-microbial agents to infected regions of humans or animals using target-specific molecules. There is a need in the art to provide methods and compositions useful for treatment of microbial organisms and microbially mediated diseases, especially microbial diseases of mucosal surfaces that are not readily accessible by normal anti-microbial mechanisms provided by the immune system.

SUMMARY OF THE INVENTION

The present invention is based on the discovery that anti-microbial peptides can be purposely directed to specific microbial organisms by a targeting moiety connected to the anti-microbial peptides. Accordingly the present invention provides a composition that has an anti-microbial effect on a targeted microbial organism. The present invention also provides methods of treating a microbial infection, e.g., on mucosal surfaces by using the compositions provided by the present invention.

In one embodiment, the present invention provides a composition useful for treatment of microbial organisms. The composition comprises a targeting moiety and an anti-microbial peptide moiety, wherein the targeting moiety is coupled to the anti-microbial peptide moiety and recognizes a target microbial organism and wherein the composition has an anti-microbial effect on the target microbial organism.

In another embodiment, the composition comprises a targeting moiety and an anti-microbial peptide moiety, wherein the targeting moiety is a peptide, e.g., polypeptide or small peptide and is fused in-frame with the anti-microbial peptide moiety. Such composition can be produced recombinantly using an expression system, e.g., bacterial, yeast, or eukaryotic cell expression system, without having to deal with problems associated with chemical or physical linkages.

In another embodiment, the present invention provides a method of treating a target microbial organism infection. The method comprises administering to a subject in need of such treatment an effective amount of the composition of the present invention.

In yet another embodiment, the present invention provides a targeting peptide comprising an amino acid sequence selected from the group consisting of SEQ ID NO. 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 45, 55, 56, 57, 58, 59, 60, and 61.

In still another embodiment, the present invention provides a targeting peptide comprising an amino acid sequence selected from the group consisting of SEQ ID NO. 24, 25, 26, 27, 28, 29, 30, 31, 32, and 33, wherein the targeting peptide specifically binds to a microorganism of *Pseudomonas*.

In yet another embodiment, the present invention provides a targeting peptide comprising an amino acid sequence selected from the group consisting of SEQ ID NO. 34, 35, 36, 37, 38, 39, 40, 41, 42, 43, 44, 45, 46, 47, 48, 49, 50, and 51, wherein the targeting peptide specifically binds to a microorganism of *Staphylococcus*.

In another embodiment, the present invention provides a targeting peptide comprising an amino acid sequence selected from the group consisting of SEQ ID NO. 52, 53, 45, 55, 56, 57, 58, 59, 60, and 61, wherein the targeting peptide specifically binds to a microorganism of *E. coli*.

SUMMARY OF THE FIGURES

FIG. 1 shows a schematic diagram of the sequential PCR reactions used to assemble the heavy chain portion of the antibody-based fusion protein.

FIG. 2 shows the sequences (SEQ ID NOS: 7-13) of the primers used in the sequential PCR reactions in embodiments of the present invention.

FIG. 3 shows the nucleotide sequence (SEQ ID NO: 1) encoding the anti-microbial peptide, histatin 5, the linker peptide, and the variable region of the heavy chain derived from the SWLA3 monoclonal antibody together with the amino acid sequence (SEQ ID NO: 2).

FIG. 4 shows the nucleotide sequence (SEQ ID NO: 3) encoding the anti-microbial peptide, dhvar 1, the linker peptide, and the variable region of the heavy chain derived from the SWLA3 monoclonal antibody together with the amino acid sequence (SEQ ID NO: 4).

FIG. 5 shows the schematic diagram of making a minibody-anti-microbial peptide fusion protein.

FIG. 6 shows killing kinetics of G10 against *Pseudomonas mendocina*.

FIG. 7 shows killing kinetics of G10CatC against *Pseudomonas mendocina*

FIG. 8 shows killing kinetics of G10CatN against *Pseudomonas mendocina*.

FIG. 9 shows killing kinetics of G10 against *Pseudomonas aeruginosa* PAK.

FIG. 10 shows killing kinetics of G10CatC against *Pseudomonas aeruginosa* PAK.

FIG. 11 shows long-term killing kinetics of G10 and G10CatC against *Pseudomonas mendocina*.

FIG. 12 shows selective killing of *Pseudomonas mendocina* by G10CatC in mixed culture.

FIG. 13 shows nonselective killing of *Pseudomonas mendocina* by G10 in mixed culture.

FIG. 14 shows selective killing of PAK by G10CatC in mixed culture.

FIG. 15 shows nonselective killing of PAK by G10 in mixed culture.

DESCRIPTION OF THE PREFERRED EMBODIMENTS

The present invention relates in general to the targeted anti-microbial effects using a composition, e.g., a chimeric construct containing a targeting moiety and an anti-microbial peptide moiety. The present invention also provides methods of treating a microbial infection using the compositions provided by the present invention.

According to the present invention, a targeting moiety can be any suitable structure that recognizes and binds to a target microbial organism. For example, a targeting moiety can be a polypeptide, peptide, small molecule, ligand, receptor, antibody, protein, or portions thereof that specifically interacts with a target microbial organism, e.g., the cell surface appendages such as flagella and pili, and surface exposed proteins, lipids and polysaccharides of a target microbial organism.

In one embodiment, the targeting moiety of the present invention is a monoclonal antibody or one of various forms of a monoclonal antibody that specifically recognizes an epitope or antigen of a target microbial organism. Such epitope or antigen usually is species-specific and located on the surface of a target microbial organism. A monoclonal antibody or various forms thereof in a targeting moiety can direct an anti-microbial peptide moiety to its target site. Furthermore, it may also provide anti-microbial effect in addition to the effect provided by the anti-microbial peptide moiety since such monoclonal antibody may engage an immune system and elicit an antibody-associated immune response, e.g., humoral immune response.

A monoclonal antibody specific to a microbial organism can be made using any methods readily available to one skilled in the art. For example, as described in the U.S. Pat. No. 6,231,857 (incorporated herein by reference) three monoclonal antibodies, i.e., SWLA1, SWLA2, and SWLA3 have been made against *S. mutans*. Monoclonal antibodies obtained from non-human animals to be used in a targeting moiety can also be humanized by any means available in the art to decrease their immunogenicity and possibly increase their ability to elicit anti-microbial immune response of a human.

Various forms of a monoclonal antibody include, without limitation, scFv, minibody, Di-miniantibody, Tetra-miniantibody, (scFv)$_2$, Diabody, scDiabody, Triabody, Tetrabody, and Tandem diabody. A scFv usually comprises a single chain containing the variable regions of a light chain and a heavy chain, optionally joined via a linker. A minibody usually comprises the variable regions of a light chain and a heavy chain, e.g., scFv joined to a heavy chain constant region, e.g., about 20 amino acids or the third constant domain, $C_H3$ domain, either directly or via a linker, e.g., about 10 to 25 amino acids. A minibody can be readily made by expressing its encoding sequence in any suitable host such as *E. coli*, yeast, or eukaryotic cell lines. A readily prepared version of a minibody usually forms a disulfide-linked dimer by virtue of the constant region, e.g., $C_H3$ domain and a cysteine-containing linker. Various forms of a monoclonal antibodies are described in Little et al., Immunology Today, 21:364-370 (2000), which is incorporated herein by reference.

Alternatively, the targeting moiety of the present invention can include all or a portion of one or more variable regions that are capable of specifically recognizing or binding to a target microbial organism and optionally a portion of constant regions that is sufficient for dimerization. For example, the variable region of a heavy chain has three complementarity determining regions (CDRs) and is capable of binding to an antigen. One skilled in the art can readily assess the minimum variable regions required of any particular monoclonal antibody for antigen or epitope binding.

According to another embodiment of the present invention, a targeting moiety can be a targeting peptide capable of specifically binding to a microorganism, e.g., a target microbial organism. In one embodiment, the targeting peptide provided by the present invention can be identified via screening peptide libraries. For example, a phage display peptide library can be screened against a target microbial organism or a desired antigen or epitope thereof. Any peptide identified through such screening can be used as a targeting peptide for the target microbial organism.

In another embodiment, the targeting peptide provided by the present invention is a peptide capable of specifically binding to *Pseudomonas*, especially *P. aeruginosa*. Such targeting peptide includes, without any limitation, a peptide containing an amino acid sequence as shown in SEQ ID NO. 24, 25, 26, 27, 28, 29, 30, 31, 32, or 33.

In yet another embodiment, the targeting peptide provided by the present invention is a peptide capable of specifically binding to *Staphylococcus*, especially *S. aureus*. Such targeting peptide includes, without any limitation, a peptide containing an amino acid sequence as shown in SEQ ID NO. 34, 35, 36, 37, 38, 39, 40, 41, 42, 43, 44, 45, 46, 47, 48, 49, 50, or 51.

In still another embodiment, the targeting peptide provided by the present invention is a peptide capable of specifically binding to *E. coli*. Such targeting peptide includes, without any limitation, a peptide containing an amino acid sequence as shown in SEQ ID NO. 52, 53, 54, 55, 56, 57, 58, 59, or 60.

According to the present invention, the targeting peptide of the present invention can also be a peptide obtained based on rational design. For example, one can design a targeting peptide based on the biochemical and biophysical characteristics of amino acids and the surfaces of microorganisms. In general, positively charged peptides are likely to bind negatively charged components on the cell surface and vice versa. Similarly, hydrophobic peptides may bind to hydrophobic pockets on the cell surface based on hydrophobic interactions while secondary or tertiary structure of a peptide may fit into certain structures on the surface of a microorganism.

In one embodiment, the targeting peptide provided by the present invention is a peptide containing an amino acid sequence as shown in SEQ ID NO. 61, 62, 63, 64, 65, 66, 67, or 68. In another embodiment, the targeting peptide provided by the present invention is a peptide containing an amino acid sequence as shown in SEQ ID NO. 61 and capable of specifically binding to *Pseudomonas*, or *E. coli*.

The targeting peptides provided by the present invention can be naturally or non-naturally occurring peptides. For example, the targeting peptides provided by the present invention can be recombinantly made, chemically synthesized, or naturally existing. In one embodiment, the targeting peptide contains an amino acid sequence that constitutes an internal part of a naturally occurring polypeptide. In another embodiment, the targeting peptide contains an amino acid sequence encoded by a sequence naturally existing in a genome and such amino acid sequence is not adjacent to any amino acid sequence naturally adjacent to it, e.g., such amino acid sequence is adjacent to a heterologous sequence in the targeting peptide.

The targeting peptide provided by the present invention can also include a peptide having an amino acid sequence that is derived or modified from a targeting amino acid sequence specifically illustrated in the present invention, provided that the derived or modified sequence still maintains or has an enhanced specificity with respect to its target microbial organism. For example, the targeting amino acid sequence can be structurally modified via deletion, mutation, addition of amino acids or other structural entities, or any other structural changes as long as these changes do not alter or adversely affect the binding ability of the targeting amino acid sequence to its target microbial organism.

In one embodiment, the modifications to the original targeting amino acid sequence do not alter its core sequence, e.g. the consensus sequence among a group of targeting amino acid sequences provided by the present invention. For example, the consensus sequence among targeting amino acid sequences of SEQ ID NO. 24, 25, 26, 27, 28, 29, 30, 31, 32, and 33 is V/Q/H-P/H-H-E-F/Y-K/H-H/A-L/H-X-X-K/R-P/L (SEQ ID NO. 14), and according to the present invention any modification to a targeting amino acid sequence of SEQ ID NO. 24, 25, 26, 27, 28, 29, 30, 31, 32, and 33 should not alter the consensus sequence contained therein, e.g., should not alter the V/Q/H-P/H-H-E-F/Y-K/H-H/A-L/H-X-X-K/R-P/L (SEQ ID NO. 14) sequence contained therein.

The targeting peptide provided by the present invention is useful for delivery of various entities to a desired locus. For example, the targeting peptide provided by the present invention can be used to deliver anti-microbial agents such as anti-microbial peptides and detectable agents such as imaging agents, which are detectable either directly or via a secondary imaging agent. For example, the detectable agent to be delivered can be an agent which can be used with an imaging technique such as magnetic resonance imaging (MRI), positron emission tomography (PET), computer-assisted tomography (CAT), X-ray, fluoroscopy and single photon emission computerized tomography.

The targeting moiety of the present invention can also be a ligand, receptor, or fragment thereof that specifically recognizes a target microbial organism. For example, the targeting moiety of the present invention can be glucan binding proteins of *Streptococcus mutans* that can specifically bind insoluble glucans on the surface of *S. mutans*.

The composition of the present invention can contain one or more targeting moieties capable of targeting the same or different target microbial organisms. In one embodiment, the composition of the present invention contains one or more targeting moieties capable of targeting different sites or structures of the same target microbial organism. Such composition is useful for preventing resistance of a target microbial organism to the composition.

According to the present invention, an anti-microbial peptide moiety of the composition of the present invention comprises one or more anti-microbial peptides. In general, any known or later discovered anti-microbial peptides can be used for the compositions of the present invention. Anti-microbial peptides are various classes of peptides, e.g., peptides originally isolated from plants as well as animals. In animals, anti-microbial peptides are usually expressed by various cells including neutrophils and epithelial cells. In mammals including human, anti-microbial peptides are usually found on the surface of the tongue, trachea, and upper intestine.

Naturally occurring anti-microbial peptides are generally amphipathic molecules that contain fewer than 100 amino acids. Many of these peptides generally have a net positive charge (i.e., cationic) and most form helical structures. It is generally believed that these peptides' anti-microbial efficacy is in their ability to penetrate and disrupt the microbial membranes, thereby killing the microbe or inhibiting its growth.

The anti-microbial activities of the anti-microbial peptides of the present invention include, without limitation, antibacterial, antiviral, or antifungal activities. For example, one well-known class of anti-microbial peptides are the tachyplesins which are described as having antifungal and antibacterial activities. Androp in, apidaecin, bactencin, clavanin, dodecappeptide, defensin, and indolicidin are anti-microbial peptides having antibacterial activities. Buforin, nisin and cecropin peptides have been demonstrated to have anti-microbial effects on *Escherichia. coli, Shigella disenteriae, Salmonella typhimurium, Streptococcus pneumoniae, Staphylococcus aureus*, and *Pseudomonas aeroginosa*. Magainin and ranalexin peptides have been demonstrated to have anti-microbial effects on the same organsims, and in addition have such effects on *Candida albicans, Cryptococcus neoformans, Candida krusei,* and *Helicobacter pylori*. Magainin has also been demonstrated to have anti-microbial effects on herpes simplex virus. Alexomycin peptides have been demonstrated to have anti-microbial effects on *Campylobacter jejuni, Moraxella catarrhalis* and *Haemophilus inflluenazae* while α defensin and β pleated sheet defensin peptides have been shown to have anti-microbial effects on *Streptococcus pneumoneae*.

Histatin peptides and the derivatives thereof are another class of anti-microbial peptides, which have antifungal and antibacterial activities against a variety of organisms including *Streptococcus mutans*. MacKay, B. J. et al., Infect. Immun. 44:695-701 (1984); Xu, et al., J. Dent. Res. 69:239 (1990).

In one embodiment, the anti-microbial peptide moiety of the present invention contains one or more anti-microbial peptides from a class of histatin peptides and the derivatives thereof. For example, the anti-microbial peptide moiety of the present invention contains one or more derivatives of histatin including, without limitation, histatin 5 having an amino acid sequence as shown in SEQ ID NO. 5 or dhvar 1 having an amino acid sequence as shown in SEQ ID NO. 6.

In another embodiment, the anti-microbial peptide moiety of the present invention contains one or more anti-microbial peptides from a class of protegrins and the derivatives thereof. For example, the anti-microbial peptide moiety of the present invention contains protegrin PG-1 having an amino acid sequence RGGRLCYCRRRFCVCVGR as shown in SEQ ID NO. 15. The protegrin peptides have been shown to have anti-microbal effects on *Streptococcus mutans, Neisseriagonorrhoeae, Chlamydia trachomatis* and *Haempohilus influenzae*. Protegrin peptides are described in the U.S. Pat. Nos. 5,693,486, 5,708,145, 5,804,558, 5,994,306, and 6,159,936, all of which are incorporated herein by reference.

In yet another embodiment, the anti-microbial peptide moiety of the present invention contains one or more anti-microbial peptides from a class of novispirin and the derivatives thereof as described in Sawai et al., "Impact of Single-Residue Mutations on the Structure and Function of Ovispirin/Novispirin Antimicrobial Peptides." *Protein Engineering* (in press). For example, the anti-microbial peptide moiety of the present invention contains novispirin G10 having an amino acid sequence KNLRRIIRKGIHIIKKYG as shown in SEQ ID NO. 16 for treating cariogenic organisms, e.g., *Streptococcus mutans*.

In still another embodiment, the anti-microbial peptide moiety contains one or more anti-microbial peptides including, without limitation, alexomycin, andropin, apidaecin, bacteriocin, β-pleated sheet bacteriocin, bactenecin, buforin, cathelicidin, α-helical clavanin, cecropin, dodecapeptide, defensin, β-defensin, α-defensin, gaegurin, histatin, indolicidin, magainin, nisin, protegrin, ranalexin, tachyplesin, and derivatives thereof.

The anti-microbial peptide moiety of the present invention can include one or more anti-microbial peptides, which can be the same or different anti-microbial peptides. The anti-microbial peptides of the present invention can also be modified, e.g., to enhance its anti-microbial effectiveness, its cell delivery, its compatibility with the rest of the composition structure, or the manipulation of the composition in production.

The targeting moiety and the anti-microbial peptide moiety of the present invention can be coupled by various means known to one skilled in the art. For example, the targeting moiety and the anti-microbial peptide moiety can be covalently coupled or connected by a peptide linker; and the composition so formed can be constructed through molecular cloning and overexpressed and purified as one polypeptide unit in a bacterial, yeast, or eukaryotic cell expression system. Any peptide linker can be used to connect the targeting moiety and the anti-microbial peptide moiety of the present invention. In one embodiment, the peptide linker does not interfere or inhibit the activity of the targeting moiety or the anti-microbial peptide moiety. In another embodiment, the peptide linker is from about 10 to 60 amino acids, from about 15 to 25 amino acids, or about 15 amino acids.

An anti-microbial peptide can be connected to a targeting moiety at either or both ends of the targeting moiety. In one embodiment, a targeting moiety is a peptide or polypeptide which can be fused in frame at N-terminal, C-terminal, or both ends with one or more anti-microbial peptides.

In another embodiment, the targeting moiety is a targeting peptide containing an amino acid sequence as shown in SEQ ID NO. 61 and is fused in frame at either end of an anti-microbial peptide, e.g., novispirin G10 as shown in SEQ ID NO. 70 and 71. In yet another embodiment, the targeting moiety is a targeting peptide containing an amino acid sequence as shown in SEQ ID NO. 61 and is fused in frame at the C-terminal end of an anti-microbial peptide, e.g., novispirin G10 as shown in SEQ ID NO. 70.

The composition of the present invention can be made by any suitable means known to one skilled in the art. For example, a nucleotide sequence encoding a targeting moiety ligated to a nucleotide sequence encoding an anti-microbial peptide moiety, either directly or via a nucleotide sequence encoding a peptide linker, can be expressed in an appropriate expression system, e.g., a commercially available bacterial, yeast, or eukaryotic cell expression system. Usually for expressing in a bacterial expression system, an autocatalytic protein, e.g., intein and a chitin-binding domain (CBD) are used for purification purpose. For expressing in a yeast expression system, a pheromone factor a is usually fused to the N-terminal of a coding sequence while a myocin-his tag is fused to the C-terminal of the coding sequence for easy handling of the expressed product during the purification process.

In one embodiment of the present invention, a commercially available yeast expression system is modified, e.g., proteins used for bacterial expression systems are used for yeast expression. For example, a sequence encoding the composition of the present invention is fused with a sequence encoding pheromone factor α and a sequence encoding intein and CBD and is expressed in a yeast expression system.

The compositions of the present invention can be used to treat any target microbial organisms. For example, the target microbial organism of the present invention can be any bacteria, rickettsia, fungi, yeasts, protozoa, or parasites. In one embodiment, the target microbial organism is a cariogenic organism, e.g., *Streptococcus mutans*.

In another embodiment, the target microbial organisms of the present invention include, without limitation, *Escherichia. coli, Candida, Salmonella, Staphylococcus,* and *Pseudomonas*, especially *Campylobacter jejuni, Candida albicans, Candida krusei, Chlamydia trachomatis, Clostridium difficile, Cryptococcus neoformans, Haempohilus influenzae, Helicobacter pylor, Moraxella catarrhalis, Neisseria gonorrhoeae, Pseudomonas aeroginosa, Salmonella typhimurium, Shigella disenteriae, Staphylococcus aureus,* and *Streptococcus pneumoniae*.

According to another feature of the present invention, the compositions of the present invention provide anti-microbial effect to target microbial organisms and can be used to treat a target microbial organism infection. An anti-microbial effect includes inhibiting the growth or killing of the target microbial organisms, or interfering with any biological functions of the target microbial organisms.

In general, the compositions of the present invention can be used to treat a target microbial organism infection at any place in a host, e.g., at any tissue including surfaces of any implant. In one embodiment, the compositions of the present invention are used to treat a target microbial organism infection on a mucosal surface or a surface containing a biofilm. A mucosal surface usually harbors a broad spectrum of microbial organisms, e.g., existing as a biofilm and prefers a treatment that is least disturbing to the balance of the entire microbial organism population, e.g., specific to pathogenic microbial organisms and has minimum effect on the non-pathogenic microbial population.

For example, in human mouth there usually exist many different microbes including yeasts and bacteria. Most of the bacteria are non-harmful commensal bacteria that are essential for maintaining a healthy and normal microbial flora to prevent the invasion and establishment of other pathogenic microbial organisms, e.g., yeast infection. Administering the composition of the present invention targets specifically to cariogenic organisms, e.g. *Streptococcus mutans* and will have minimum effect on non-targeted microbial organisms, thus will not have an undesirable effect by non-targeted microbial organisms.

Many places in an animal or human body have mucosal surfaces colonized by multiple species microbial biofilms and can be treated with the compositions of the present invention to provide targeted anti-microbial effect. For example, mouth, vagina, gastrointestinal (GI) tract, esophageal tract, respiratory tract, implants, all of which can have microbial organism infection on its mucosal surfaces.

In particular, *S. mutans* infection is commonly found in mouth and causes. dental caries. *Porphyromonas gingivalis*, various Actinomyces species, *Veillonella, spirochetes*, and black-pigmented bacteroides are commonly associated with infections of gingival and surrounding connective tissues, which cause periodontal diseases. *Streptococcus pneumoniae*, nontypeable *Haemophilius influenza*, or *Moraxella cararrhalis* infection is commonly found in acute otitis media (AOM) and otitis media effusion (OME) as complications of upper respiratory infections in young children.

*Helicobacter pylori* (*H. pylori*) bacteria are found in the gastric mucous layer or adherent to the epithelial lining of the stomach, and cause more than 90% of duodenal ulcers and up to 80% of gastric ulcers. Other GI tract infections include, without limitation, campylobacter bacterial infection, primarily *Campylobacter jejuni* associated with diarrhea, cholera caused by *Vibrio cholerae* serogroups, salmonellosis caused by bacteria salmonella such as *S. Typhimurium* and *S. enteritidis*, shigellosis caused by bacteria *Shigella*, e.g., *Shigella dysenteriae* and traveler's diarrhea caused by enterotoxigenic *Escherichia coli* (ETEC). *Clostridium difficile* infection is also commonly found in gastrointestinal tract or esophageal tract.

*Pseudomonas* organisms have been associated with common-source nosocomial outbreaks; in addition, they have been incriminated in bacteremia, endocarditis, and osteomyelitis in narcotic addicts. Infections with *Pseudomonas* organisms can also occur in the ear, lung, skin, or urinary tract of patients, often after the primary pathogen has been eradicated by antibiotics. Serious infections are almost invariably associated with damage to local tissue or with diminished host resistance. Patients compromised by cystic fibrosis and those with neutropenia appear at particular risk to severe infection with *P. aeruginosa*. Premature infants; children with congenital anomalies and patients with leukemia; patients with burns; and geriatric patients with debilitating diseases are likely to develop *Pseudomonas* infections. The organism is prevalent in urine receptacles and on catheters, and on the hands of hospital staff.

The *staphylococci*, of which *Staphylococcus aureus* is the most important human pathogen, are hardy, gram-positive bacteria that colonize the skin of most human beings. If the skin or mucous membranes are disrupted by surgery or trauma, staphylococci may gain access to and proliferate in the underlying tissues, giving rise to a typically localized, superficial abscess. Although these cutaneous infections are most commonly harmless, the multiplying organisms may invade the lymphatics and the blood, leading to the potentially serious complications of staphylococcal bacteremia.

These complications include septic shock and serious metastatic infections, including endocarditis, arthritis, osteomyelitis, pneumonia, and abscesses in virtually any organ. Certain strains of *S. aureus* produce toxins that cause skin rashes or that mediate multisystem dysfunction, as in toxic shock syndrome. Coagulase-negative staphylococci, particularly *S. epidermidis*, are important nosocomial pathogens, with a particular predilection for infecting vascular catheters and prosthetic devices. *S. saprophyticus* is a common cause of urinary tract infection.

*Yeast* or *Candida* infections (Candidiasis) typically occur either orally (Oropharyngeal Candida or OPC) or vaginally (Vulvovaginal Candida or VVC). Candidiasis is caused by a shift in the local environment that allows Candida strains (most commonly *Candida albicans*) already present on skin and on mucosal surfaces such as mouth and vagina to multiply unchecked. Gonorrhea, chlamydia, syphilis, and trichomoniasis are infections in the reproductive tract, which cause sexually transmitted diseases, e.g., pelvic inflammatory disease.

The compositions of the present invention can be administered to various mucosal or biofilm surfaces, e.g., the mucosal surfaces described above, with each composition containing a targeting moiety corresponding to one or more specific microbial organisms of the infection, e.g., the microbial organisms described above.

The composition of the present invention can also be administered to various biofilm surfaces outside of a human body, e.g., industrial applications. For example, in food processing industry the composition of the present invention can be administered to food processing equipments or food itself to prevent infections related to food consumption, e.g., *Salmonella* in a poultry processing facility.

The compositions of the present invention useful for treating target microbial organism infection can be administered alone, in a composition with a suitable pharmaceutical carrier, or in combination with other therapeutic agents. An effective amount of the compositions to be administered can be determined on a case-by-case basis. Usually the dosage required is lower than the dosage required for an anti-microbial peptide administered without being linked to a targeting moiety, e.g., $10^{-1}$ lower. Factors to be considered usually include age, body weight, stage of the condition, other disease conditions, duration of the treatment, and the response to the initial treatment.

Typically, the compositions are prepared as a topical or an injectable, either as a liquid solution or suspension. However, solid forms suitable for solution in, or suspension in, liquid vehicles prior to injection can also be prepared. The composition can also be formulated into an enteric-coated tablet, gel capsule or microsphere formulation according to known methods in the art.

The compositions of the present invention may be administered in any way which is medically acceptable which may depend on the disease condition or injury being treated. Possible administration routes include injections, by parenteral routes such as intravascular, intravenous, intraepidural or others, as well as oral, nasal, ophthalmic, rectal, topical, or pulmonary, e.g., by inhalation. The compositions may also be directly applied to tissue surfaces. Sustained release, pH dependent release, or other specific chemical or environmental condition mediated release administration is also specifically included in the invention, by such means as depot injections or erodible implants.

In one embodiment, the compositions of the present invention are used to treat or prevent cariogenic organism infections, e.g., S. mutans infection associated with dental caries and are prepared as additives to food or any products having direct contact to an oral environment, especially an oral environment susceptible to dental caries. For example, to treat or prevent dental caries one or more compositions of the present invention can be formulated into a baby formula, mouthwash, lozenges, gel, varnish, toothpaste, toothpicks, tooth brushes, or other tooth cleansing devices, localized delivery devices such as sustained release polymers or microcapsules, oral irrigation solutions of any kind whether mechanically delivered or as oral rinses, pacifiers, and any food including, without limitation, chewing gums, candies, drinks, breads, cookies, and milk.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1

Construction and Expression of a Histatin 5 and Dhvar 1/SWLA3 Chimeric Antibody Fusion Protein with Activity Against *S. mutans* a. Construction of an Expression Vector for an Antibody-based Fusion Protein

The construct that is ultimately cloned into an IgG$_1$ expression vector and leads to the expression of the targeted antimicrobial fusion protein was assembled according to the following method (see FIG. 1). The construct was assembled using sequential PCR and restriction enzymes techniques. The recognition sequence of the fusion protein was derived from heavy chain sequences of SWLA3, produced by hybridoma ATCC HB 12558. See Shi, U.S. Pat. No. 6,231,857, the disclosure of which is incorporated herein by reference, and U.S. patent application Ser. Nos. 09/378,577 and 09/881,823. Sequences encoding histatin 5 or dhvar1 were inserted upstream of the variable region of the heavy chain of SWLA3. The amino acid sequences used for histatin 5 and dhvar 1 are listed below:

```
Histatin  (SEQ ID NO: 5) DSHAKRHHGY KRKFHEKHHS HRGY
5
Dhvar 1   (SEQ ID NO: 6) KRLFKELKFS LRKY.
```

The source signal peptide was added upstream of the histatin 5 or dhvar1, and a glycine/serine linker was added to separate the fusion protein from the variable region of the heavy chain (V$_H$) of the antibody. See FIG. 3 for the nucleic acid and encoded amino acid sequence for the histatin 5/SWLA3 V$_H$ and FIG. 4 for the respective dhvar 1/SWLA3 V$_H$ sequences. Sequential PCR reactions were used to complete the construct according to the following method (see FIG. 2 for the nucleic acid sequence of the primers used):

1. In the first PCR reaction a plasmid carrying the V$_H$ of SWLA3 was used as the template with primer sets 986+452 (histatin 5) or 989+452 (dhvar1). This reaction replaced the signal peptide in the original gene with the linker peptide at the 5' end of the VH and inserted a restriction site at the 3' end. The products of this reaction were isolated and used as a template in the second PCR reaction.

2. Using primer sets 987+452 (histatin 5) or 990+452 (dhvar1) in the second PCR reaction added the anti-microbial peptide upstream from the linker peptide. The restriction site at the 3' end was maintained. The products from this reaction were isolated and used as the template in the third PCR reaction.

3. With primer sets 988+452 (histatin 5) or 991+452 (dhvar1) a signal peptide and restriction site were added upstream from the anti-microbial peptide. The restriction site at the 3' end was maintained. Products from the third PCR were isolated.

4. Isolated products from the third PCR reaction were then cloned into Invitrogen's PCR2.1 vector via TOPO Cloning Kit and sequenced.

5. After the sequences of the two clones were confirmed, the inserts were moved into the IgG$_1$ PCR expression vector (pAH 4604) as an NheI/EcoRV fragment.

6. The final expression vectors for the histatin 5 and dhvar 1 antibody fusion proteins were named pAH 5993 and pAH 5994 respectively.

PCR conditions used were:

1. Denature @ 94° C. for 40 sec.
2. Anneal @ 60° C. for 40 sec.
3. Extend @ 72° C. for 40 sec.
4. Amplify for 30 cycles
5. Final Extension at 72° C. for 10 min.

FIG. 3 shows the nucleic acid sequence encoding the histatin 5 fusion to V$_H$ SWLA3 and encoded amino acid sequence (SEQ ID NOS: 1 and 2) and FIG. 4 which shows the nucleic acid sequence encoding the dhvar1 fusion to V$_H$ SWLA3 and encoded amino acid sequence (SEQ ID NOS: 3 and 4). In the figures, the bold sequences represent the corresponding anti-microbial peptides, the underlined sequences represent the glycine/serine linker, and the single bolded underlined base in each sequence represents a silent point mutation. In the original sequence disclosed in Shi et al. U.S. patent application Ser. No. 09/881,823, the base is guanine.

The variable region of the light chain (V$_L$) from SWLA3 was cloned into a human kappa expression vector named 5940 pAG according to the method described in Shi et al. U.S. patent application Ser. No. 09/881,823. Briefly, (i) DNA was prepared from the expression vectors and from the plasmid containing the correct V$_L$. See Current Protocols in Immunology, Section 2.12.1 (1994) for detailed information about the vectors that express the light and heavy chain constant regions.

(ii) The expression vector was digested with the appropriate restriction enzyme. The digests were then electrophoresed on an agarose gel to isolate the appropriate sized fragment.
(iii) The plasmid containing the cloned $V_L$ region was also digested and the appropriate DNA fragment containing the $V_L$ region was isolated from an agarose gel.
(iv) The $V_L$ region and expression vector were then mixed together, T4 DNA ligase was added and the reaction mixture was incubated at 16° C. over night.
(v) Competent cells were transfected with the $V_L$ ligation mixture and the clones expressing the correct ligation sequence were selected. Restriction mapping was used to confirm the correct structure.

b. Transfecting Eukaryotic Cells

Ten micrograms of DNA from each expression vector, pAH 5993 (histatin 5) or pAH 5994 (dhvar 1) and 5940 pAG, was linearized by BSPC1 (Stratagene, PvuI isoschizomer) digestion and $1 \times 10^7$ myeloma cells (SP2/0 or P3x63. Ag8.653) were cotransfected by electroporation. Prior to transfection the cells were washed with cold PBS, then resuspended in 0.9 ml of the same cold buffer and placed in a 0.4 cm electrode gap electroporation cuvette. 960 microF and 200V was used for electroporation. The shocked cells were then incubated on ice in IMDM medium (Gibco, N.Y.) with 10% calf serum.

The transfected cells were plated into 96 well plates at a concentration of 10000 cells/well. Selective medium including selective drugs such as histidinol or mycophenolic acid were used to select the cells which contain expression vectors. After 12 days, the supernatants from growing clones were tested for antibody production.

c. Analyses of Histatin-5 and dhvar 1/SWLA3 Chimeric Antibody Fusion Proteins

ELISA assay was used to identify transfectomas that secrete the fusion IgG antibodies. 100 μl of 5 μg/ml goat anti-human IgG was added to each well of a 96-well ELISA plate and incubated overnight. The plate was washed several times with PBS and blocked with 3% BSA. Supernatants from above growing clones were added to the plate for 2 hours at room temperature to assay for their reactivity with goat anti-human Ig antibody. Plates were then washed and anti-human kappa antibody labeled with alkaline phosphatase diluted $1:10^4$ in 1% BSA was added for 1 hour at 37° C. Plates were washed with PBS and para-nitrophenyl phosphate in diethanolamine buffer (9.6% diethanolamine, 0.24 mM $MgCl_2$, pH 9.8) was added. Color development at $OD_{405}$ was indicative of cells producing $H_2L_2$.

For the supernatants that produce IgG constant regions, their reactivity with S. mutans was tested as described in Shi et al., Hybridoma 17:365-371 (1998). Briefly, bacteria strains listed in Table 1 were grown in various media suggested by the American Type Culture Collection. The anaerobic bacteria were grown in an atmosphere of 80% $N_2$, 10% $CO_2$, and 10% $H_2$ at 37° C. The specificity of antibodies to various oral bacteria was assayed with ELISA assays. Bacteria were diluted in PBS to $OD_{600}$=0.5, and added to duplicate wells (100 μl) in 96 well PVC ELISA plates preincubated for 4 h with 100 μl of 0.02 mg/ml Poly-L-lysine. These antigen-coated plates were incubated overnight at 4° C. in a moist box then washed 3 times with PBS and blocked with 0.5% fetal calf serum in PBS and stored at 4° C. 100 μ l of chimeric antibodies at 50 μg/ml were added to the appropriate wells of the antigen plates, incubated for 1 h at RT, washed 3 times with PBS-0.05% Tween 20, and bound antibody detected by the addition of polyvalent goat-anti-human IgG antibody conjugated with alkaline phosphatase diluted $1:10^3$ with PBS-1% fetal calf serum. After the addition of the substrate, 1 mg/ml p-nitrophenyl phosphate in carbonate buffer (15 mM $Na_2CO_3$, 35 mM $NaH_2CO_3$, 10 mM $MgCl_2$ pH 9.6), the color development after 15 min was measured in a EIA reader at 405 nm. "+" means OD405>1.0; "−" means OD405<0.05. The negative control is <0.05. The results are given in Table 1.

TABLE 1

Reactivity of Antibody Fusion Proteins to Various Oral Bacterial Strains

| Oral Bacteria | Strains | Hitstatin 5/SWLA3 Fusion Antibodies | Dhvar 1/SWLA3 Fusion Antibodies |
| --- | --- | --- | --- |
| S. mutans | AATCC25175 | + | + |
|  | LM7 | + | + |
|  | OMZ175 | + | + |
| S. Mitis | ATCC49456 | − | − |
| S. rattus | ATCC19645 | − | − |
| S. sanguis | ATCC49295 | − | − |
| S sobrinus | ATCC6715-B | − | − |
| S. sobrinus | ATCC33478 | − | − |
| L. acidophilus | ATCC4356 | − | − |
| L. casei | ATCC11578 | − | − |
| L. plantarum | ATCC14917 | − | − |
| L. salivarius | ATCC11742 | − | − |
| A. actinomycetemcomitans | ATCC33384 | − | − |
| A. naeslundi | ATCC12104 | − | − |
| A. viscosus | ATCC19246 | − | − |
| Fusobacterium nucleatum | ATCC25586 | − | − |
| Porphyromonas gingivalis | ATCC33277 | − | − |

The fusion proteins showed both specificity and anti-microbial efficacy against S. mutans. Like the monoclonal antibodies from which they are derived, the fusion proteins bind specifically to S. mutans. (See Table 1). They also have antibacterial efficacy against the bacteria, but are effective at a much lower concentration than histatin 5 alone. (See Table 2).

TABLE 2

Recombinant Histatin5/SWLA3 fusion antibodies targets S. mutans with a great sensitivity and specificity
Minimal Inhibitory Concentrations

|  | S. mutans | S. sanguis | Host cells |
| --- | --- | --- | --- |
| Histatin5 | ~10 μM | ~10 μM | >50 μM |
| Histatin 5/SWLA3 fusion antibodies | ~0.3 μM | ~30 μM | >50 μM |

This observation suggests that the recognition sequence is responsible for specific binding between the fusion protein and S. mutans, which locally enhances the concentration of histatin 5 at the bacterial cell surface. At the concentration at which the fusion protein showed antibacterial efficacy, the fusion proteins showed no inhibitory effect on other bacteria or host cells (Table 2). Accordingly, these results suggest that the basic design described herein may be useful for generating antibody-based fusion proteins for treatment of other infections and infestations.

Example 2

Construction of a Chimeric Construct Containing Minibody and Anti-microbial Peptide, and its Expression in Yeast a. Construction of SWLA3 Minibody-PG-1 Peptide Fusion Protein A minibody is a modified antibody molecule that comprises of the variable regions of the heavy and light chain ($V_H$ and $V_L$) covalently linked via a short linker in a head-to-tail fashion (see FIG. 5). To construct the SWLA3 minibody-PG-1 anti-microbial peptide fusion, PG-1 was linked to the N-terminus of $V_H$ via a poly serine-glycine linker peptide, $(SGGGG)_3$(SEQ ID NO. 17). The C-terminus of $V_H$ was connected via a short GS linker, $(GGGS)_2$(SEQ ID NO. 18), to the N-terminus of $V_L$.

The starting material for constructing the minibody was the anti *S. mutans* monoclonal antibody, SWLA3, as described in the U.S. Pat. No. 6,231,857. The anti-microbial peptide was protegrin PG-1 as described in the U.S. Pat. Nos. 5,693,486, 5,708,145, 5,804,558, 5,994,306, and 6,159,936 and Zhao et al., FEBS lett, 1994, 346 (2-3): 285-8.

The coding region of the protegrin PG-1 has the following sequence: 5'-CGT GGC GGT CGC CTA TGC TAC TGT CGA CGT CGC TTT TGC GTA TGC GTG GGA CGG TCT-3' (SEQ ID NO. 19). The gene was amplified and fused with the linker region then to the VH region of SWLA3 in the same fashion as described in Example 1 for Histadin5 fusion to SWLA3.

To construct PG-1-SWLA3 minibody, the PG-1-$V_H$ fragment was amplified by PCR using primers PG-1F: 5'-GG-GAATTCCGTGGCGGTCGCCTATGCTAC-3' (SEQ ID NO. 20), and VhR2: 5'-AGAGCCGCCACCCGAACCTC-CGCCTGAAGAGACGGTGACTGAGG-3' (SEQ ID NO. 21). The $V_L$ fragment was also amplified by PCR using primers $V_L$F2: 5'-GGTTCGGGTGGCGGCTCTGATGTTGT-GATGACCCAGACT-3' (SEQ ID NO. 22), and $V_L$R2: 5'-GGTCTAGATTCCCAGAACCCCCACCCT-TACGTTTCAGCTCCAGCTTG-3' (SEQ ID NO. 23). The PG-1-$V_H$ and $V_L$ fragments were then joined by a second PCR utilizing the complementarities between the 3' portion of the PG-1-$V_H$ fragment and the 5' portion of the $V_L$ fragment. The joined fragment was amplified by PCR using primers PG-1F and $V_L$R2. The fragment was subsequently cloned into a cloning vector, pTOPO, and the correct sequence confirmed by DNA sequencing.

b. Expression of PG-1-SWLA3 Minibody Fusion in the Yeast *Pichia pastoris*.

Yeast *Pichia pastoris* is a commercially available system for over expression of a large number of proteins including antibodies and minibodies. To overexpress the PG-1-SWLA3 minibody fusion protein in *Pichia*, the PG-1-$V_H$-$V_L$ fragment was cloned into the expression vector, pPICZαA at the Eco RI-Xba I sites. The cloning resulted in fusion of the N-terminus of PG-1 with the C-terminus of the α-factor signal sequence in the vector, thus allowing secretion of the fusion protein to the outside medium. The cloning also resulted in the fusion of the C-terminus of $V_L$ to the N-terminus of the c-myc epitope and the His-tag in the vector, allowing detection and purification of the secreted protein. The construct was amplified in *E. coli*, confirmed by sequencing, and transferred into *Pichia*. The correct expression of the fusion protein was confirmed by Western blot analysis, as well as by its ability to bind specifically to *S. mutans*, the target bacteria of the original antibody SWLA3.

Example 3

Construction of Chimeric Construct Containing Surface-binding Peptide and Anti-microbial Peptide In addition to antibodies, some small peptide can also bind to surface structures of microorganisms or eukaryotic cells. These peptides, which we term "docking moiety", allow more flexibility for the antimicrobial peptides (the killing moiety) to insert into the cell membrane for killing. These peptides can be selected from phage display libraries that contain random peptide sequences. Phage-display libraries of 8-12 amino acids peptide are commercially available. In this experiment, we have screened these libraries for peptides capable of specifically binding to a target organism, which can be bacteria, yeast, or other fungi. One or more of these peptides will then be fused to the anti-microbial peptide via a peptide linker, and expressed in an appropriate host, or chemically synthesized.

a. Selection of Species-specific Binding, Peptides with Phase Display

We employed three phage display peptide libraries (New England Biolabs) that contain >$10^9$ unique random-peptide-sequence-containing phage clones. The Ph.D.-C7C library displays 7-mer peptides with disulfide linkages, while the Ph.D.-7 and Ph.D.-12 libraries contain completely randomized 7-mer and 12-mer residues, respectively. The M13 filamentous phage used for the procedure carried the random insert as an N-terminal fusion to the minor coat protein pIII.

Briefly, $10^{10}$ pfu/ml of phage library was incubated with $10^9$ bacterial cells for which targeting peptides are desired. After centrifugation, unbound phage was removed by aspiration. The pellet, which contained the target bacteria with the bound phage, was washed several times using buffers containing mild detergent to remove loosely bound phage particles, and the tightly bound phage particles were eluted. This process is termed panning.

The eluted phage was amplified by infecting *E. coli* F+ strains. After 3-4 rounds of panning and amplification, a phage pool was obtained, which contained clones with high binding affinity for the bacteria that it was panned against. Ten to twenty phage clones from this pool were randomly picked for DNA sequencing, from which the amino acid sequence of the peptide insert was determined. By aligning the amino acid sequence of multiple clones from the same phage pool, a consensus sequence for the binding peptide was constructed. This consensus sequence represents one of the binding peptides for this particular bacterium.

To confirm the binding specificity of the consensus peptide, the peptide was chemically synthesized and conjugated to FITC, a green fluorescence dye. The labeled peptide was incubated with the bacteria and analyzed by fluorescent microscopy for bacterial species-specific binding. This methodology ensured that peptides selected from phage display exhibits the same binding specificity as a free peptide independent of the M13 phage particle.

a-1. Generation of Pseudomonas Specific Binding Peptides Using Phage Display

Phage display technology was used as described above to generate targeting peptides against *Pseudomonas*. After panning against *P. aeruginosa* strain PAK cells, significant enrichment was obtained with the PhD-12 library, compared to the other libraries, after 3 rounds of panning (2 logs higher pfu/ml). A further 4th round of panning was carried out using more stringent washing conditions to select for only the tightest binding clones, and the titer of recovered bound phage for PhD-12 ($4.5 \times 10^7$ pfu/ml) remained high (Table 3). Ten clones were then selected from the recovered PhD-12 library phage after rounds 3 and 4. The sequences of the 3rd round clones are shown in Table 4.

TABLE 3

Panning of PhD-12, PhD-7 and PhD-C7C

| Library | 1st Round (pfu/ml) input | output | 2nd Round (pfu/ml) input | output | 3rd Round (pfu/ml) input | output | 4th Round (pfu/ml) input | output |
|---|---|---|---|---|---|---|---|---|
| PhD-12 | $1 \times 10^{10}$ | $4. \times 10^5$ | $3 \times 10^{10}$ | $3 \times 10^5$ | $2 \times 10^{10}$ | $2 \times 10^9$ | $1 \times 10^{10}$ | $4.5 \times 10^7$ |
| PhD-7 | $5 \times 10^{10}$ | $3 \times 10^6$ | $3 \times 10^{10}$ | $2 \times 10^4$ | $1 \times 10^{10}$ | $2 \times 10^7$ | $7 \times 10^9$ | $1 \times 10^5$ |
| PhD-C7C | $1 \times 10^{10}$ | $1 \times 10^6$ | $3 \times 10^{10}$ | $3 \times 10^4$ | $3 \times 10^{10}$ | $6 \times 10^6$ | $1 \times 10^{11}$ | $1 \times 10^5$ |

TABLE 4

Round 3 clones from PhD-12

| PhD-12 clone | Sequence | |
|---|---|---|
| 12:1 | V P H E F K H L Q M K P | SEQ ID NO: 24 |
| 12:2 | V P H E F K H L Q M K P | SEQ ID NO: 24 |
| 12:3 | H H H K A L A P T V T G | SEQ ID NO: 26 |
| 12:4 | V P H E F H A H R G R L | SEQ ID NO: 27 |
| 12:5 | V P H E F K H L Q M K P | SEQ ID NO: 24 |
| 12:6 | Q P H P H K V H S L P P | SEQ ID NO: 29 |
| 12:7 | V P H E F H A H R G R L | SEQ ID NO: 27 |
| 12:8 | V P H E F H A H R G R L | SEQ ID NO: 27 |
| 12:9 | H H L H Y N P A F P G L | SEQ ID NO: 32 |
| 12:10 | Q P A P Y I S S P S A S | SEQ ID NO: 33 |

Of the 3rd round sequences recovered, clones 12:1, 12:2, and 12:5 were identical, as well as clones 12:4, 12:7, and 12:8. These clones were probably originated from two clones. These two original clones, though not identical, share sequences at the N-terminal half of the peptide. Thus, a consensus sequence could be deduced from this peptide pool.

a-2. Generation of Specific Binding Peptide Against *Staphylococcus aureus* and *E. coli* from Phage Display Libraries.

Phage display technology was also used to generate peptides specific for *S. aureus* and *E. coli*. The PhD-12 library was used for the selections. The peptide sequences from the enriched clones are summarized in Table 5 (against *S. aureus*) and Table 6 (against *E. coli*).

TABLE 5

Amino acid sequences of clones generated against *S. aureus*

| Clone | | | | Sequence | |
|---|---|---|---|---|---|
| SA5.1 | V | R | L | P L W L P S L N E | SEQ ID NO: 34 |
| SA5.3 | A | N | Y | F L P P V L S S S | SEQ ID NO: 35 |
| SA5.4 | S | H | P | W N A Q R E L S V | SEQ ID NO: 36 |
| SA5.5 | S | V | S | V G M R P M P R P | SEQ ID NO: 37 |
| SA5.6 | W | T | P | L H P S T N R P P | SEQ ID NO: 38 |
| SA5.7 | S | V | S | V G M K P S P R P | SEQ ID NO: 39 |
| SA5.8 | S | V | S | V G M K P S P R P | SEQ ID NO: 39 |
| SA5.9 | S | V | P | V G P Y N E S Q P | SEQ ID NO: 41 |
| SA5.10 | W | A | P | P L F R S S L F Y | SEQ ID NO: 42 |
| SA2.2 | W | A | P | P X P X S S L F Y | SEQ ID NO: 43 |
| SA2.4 | H | H | G | W T H H W P P P P | SEQ ID NO: 44 |
| SA2.5 | S | Y | Y | S L P P I F H I P | SEQ ID NO: 45 |
| SA2.6 | H | F | Q | E/N P L S R G G E L | SEQ ID NO: 46 |
| SA2.7 | F | S | Y | S P T R A P L N M | SEQ ID NO: 47 |
| SA2.8 | S | X | P | X X M K X S X X X | SEQ ID NO: 48 |
| SA2.9 | V | S | R | H Q S W H P H D L | SEQ ID NO: 49 |
| SA2.10 | D | Y | X | Y R G L P R X E T | SEQ ID NO: 50 |
| SA2.11 | S | V | S | V G M K P S P R P | SEQ ID NO: 51 |

TABLE 6

Amino acid sequences of clones generated against *E. coli*

| Clone | | | | Sequence | |
|---|---|---|---|---|---|
| DH5.1 | K | H | L | Q N R S T G Y E T | SEQ ID NO. 52 |
| DH5.2 | H | I | H | S L S P S K T W P | SEQ ID NO. 53 |
| DH5.3 | T | I | T | P T D A E M P F L | SEQ ID NO. 54 |
| DH5.4 | H | L | L | E S G V L E R G M | SEQ ID NO. 55 |
| DH5.5 | H | D | R | Y H I P P L Q L H | SEQ ID NO. 56 |
| DH5.6 | V | N | T | L Q N V R H M A A | SEQ ID NO. 57 |
| DH5.7 | S | N | Y | M K L R A V S P F | SEQ ID NO. 58 |
| DH5.8 | N | L | Q | M P Y A W R T E F | SEQ ID NO. 59 |
| DH5.9 | Q | K | P | L T G P H F S L I | SEQ ID NO. 60 |

These results suggest that these species may have multiple targets on the cell surface.

b. Rational Design of Targeting Peptides Based on Biochemical/biophysical Characteristics of Amino Acids and Bacterial Surfaces In addition to phage display, potential targeting peptides can also be designed based on the biochemical and biophysical characteristics of amino acids and the bacterial cell wall. For example, positively charged peptide may bind to negatively charged components on the cell surface and vice versa. Similarly, hydrophobic peptides may bind to some hydrophobic pockets on the cell surface based on hydrophobic interactions, or some peptide may form a certain secondary structure that would fit into some structures on the cell surface. By applying these principles, we designed a panel of peptides and tested their binding potential against a panel of Gram-positive and Gram-negative bacteria.

b-1. Design of Peptide

Peptide Cat-1 contained all cationic residues so that it could potentially bind to negatively charged molecules on bacterial surfaces. Phob-1 was made to be largely hydrophobic and attracted to the hydrophobic cell wall constituents of Gram-positive bacteria. LPTG-1 contained two "cell wall binding" repeats separated by a flexible linker. These cell wall binding repeats are specifically recognized by some streptococci and are involved in bacterial adherence to surfaces. LPSB-1 and 2 consisted of repeats of the LPS binding domains found in the sheep defensin SMAP-29. Targeting peptide α-1 was designed to be 100% α-helical, a characteristic common to many characterized antimicrobial peptides and an important structural feature for insertion into bacterial membranes. Anion-1 contained all negatively charged amino acid residues while Philic-1 mainly consisted of hydrophilic amino acid residues. Peptides were synthesized by standard FastMoc chemistry.

b-1. Some representatives of designed targeting peptides

```
Cat-1                    LPSB-1

KKHRKHRKHRKH             RGLRRLGRRGLRRLGR 12 aa (SEQ ID NO. 61)    16 aa (SEQ ID NO. 62)

Phob-1                   LPSB-2

KPVLPVLPVLPVL            VLRIIRIAVLRIIRIA 12 aa (SEQ ID NO. 63)    16 aa (SEQ ID NO. 64)

LPTG-1                   α-1

LPETGGSGGSLPETG          RAHIRRAHIRR 17 aa (SEQ ID NO. 65)    11 aa (SEQ ID NO. 66)

Anion-1                  Philic-1

DEDEDDEEDDDEEE           STMCGSTMCGSTMCG 14 aa (SEQ ID NO. 67)    15 aa (SEQ ID NO. 68)
``` b-2. Testing Binding Activity of the Designed Targeting Peptides

Presented here are some examples for testing the specificity of the designed targeting peptides. The peptides were labeled at the N-terminus with the fluorescent dye FITC, and the labeled peptides were allowed to bind to the bacteria as described previously. Fluorescent microscopy was then used to determine the binding efficiency based on the brightness of the bacterial cells after peptide binding.

TABLE 7

Specificity of targeting peptides against log phase cells

| Bacterial strains | LPTG-1 | Cat-1 | Phob-1 | Dye alone |
|---|---|---|---|---|
| *E. coli* Aw405 | − | + | − | − |
| *E. coli* DH5α | − | ++ | − | − |
| *E. coli* ER2738 | − | ++ | − | − |
| *E. coli* W3110 | + | ++ | − | − |
| *E. coli* Mg1655 | − | + | − | − |
| *P. aeruginosa* Pak | − | ++++ | − | − |
| *P. mendocina* | − | ++++ | − | − |
| *S. mutans* | − | − | − | − |
| *S. epidermidis* | + | − | − | − |
| *S. aureus* | + | − | − | − |
| *T. denticola* | − | − | − | − |
| *M. xanthus* | − | − | − | − |

Data presented in Table 7 clearly show that Cat-1 binds specifically to *Pseudomonas* and *E. coli* with a much stronger binding to the former species. In contrast, Phob-1 did not bind to any of the bacterial species that we tested. LPTG-1, on the other hand, showed weak binding to the two staphylococcal species.

To further confirm the specificity of Cat-1 binding to Pak cells, competition-binding experiments were conducted. Labeled Cat-1 was mixed with increasing concentrations of unlabeled Cat-1, and fluorescent labeling of the target bacterial cells was measured by fluorescent microscopy. The results demonstrated that fluorescent signal of labeled Cat-1 on PAK cells was reduced upon addition of equal molar concentration of unlabeled Cat-1, and completely abolished at 10×molar excess unlabeled Cat-1.

c. Construction of a Species-specific Antimicrobial Peptide with High Specificity, Sensitivity, and Much Improved Killing Kinetics.

With the successful design of a targeting peptide (CAT-1) that can specifically bind to *Pseudomonas* and to *E. coli* to a lesser degree, one can fuse this targeting peptide to a non-specific antimicrobial peptide, making it a species-specific killing peptide. Below is an example for constructing such a species-specific antimicrobial peptide and testing its specificity and killing efficiency against its targeting bacteria. This example demonstrates that this novel technology can be used to develop targeted antimicrobial therapy against other pathogenic bacteria, fungi, and viruses.

c-1. Design of the Fusion Peptides

Novispirin G10 is a wide-spectrum antimicrobial peptide, which is active against both Gram-positive and Gram-negative bacteria. Two forms of the fusion peptides were constructed. G10CatC contained the targeting peptide Cat-1 domain fused at its C-terminus to G10 through a five-residue linker, GGSGG (SEQ ID NO. 69), to allow flexibility of the targeting and killing domains. G10CatN had an opposite configuration as G10CatC in that the killing domain G10 was at the N-terminal portion of the fusion peptide. The sequences of the two fusion peptides are shown below.

G10CatC

KKHRKHRKHRKHGGSGGSKNLRRIIRKGIHIIKKYG (SEQ ID NO. 70)

Cat-1 domain        G10 domain

G10CatN

KNLRRIIRKGIHIIKKYGGGSGGSKKHRKHRKHRKH (SEQ ID NO. 71)

G10 domain        Cat-1 domain c-2. Determination of the Minimum Bactericidal Concentration (MBC) of the Fusion Peptides To test the antimicrobial activity of the fusion peptides against target bacteria, a panel of bacteria, both gram positive and gram negative, were tested. The results of the minimum bactericidal concentration (MBC) are summarized in Table 8.

TABLE 8

MBCs of G10, G10CatC and G10CatN against a selected panel of bacteria

| Bacteria | MBC (μM) | | |
|---|---|---|---|
|  | G10 | G10C | G10N |
| Salmonella Lt2 (ATCC) | >22.5 | 11.6-23.2 | >23.2 |
| Salmonella Lt7 | >22.5 | >23.2 | >23.2 |
| E. coli 3132 (wt) | 11.25 | 5.8 | 11.6 |
| E. coli W3110 | 1.4 | 2.81 | >11.6 |
| E. coli W3110 ampR | 2.8 | 2.9 | >23.2 |
| E. coli Aw405 | 2.8 | 11.6 | >23.2 |
| E. coli Mg1665 (smooth) | 2.8 | 2.9 | >23.2 |
| P. mendocina | 1.05 | 1.4-2.4 | 2.8 |
| P. aeruginosa Pak (ATCC) | 42.18 | 4.9 | 17.4 |
| P. aeruginosa Pak | 54.5 | 1.4-2.9 | 45 |
| P. fluorescens 1088 | 1.4 | 1.45 | 1.45 |
| P. fluorescens 1089 | >11.25 | 2.9 | 11.6 |
| P. tabaci | 5.625 | 2.175 | >11.6 |
| B. cepacia | 23 | 13 | 11.6 |
| Y. entercolitica | 22.5 | 23.2 | >23.2 |
| Myxococcus | >11.25 | >11.6 | >11.6 |
| Klebsiella Kay2026 | >11.25 | 11.6-23.2 | >11.6 |
| S. aureus | >22.5 | >23.2 | >23.2 |
| S. mutans 140 | 3.5-7.03 | 3.6-7.25 | ND |
| S. mutans 159 | 3.5-7.03 | 3.6-7.25 | ND |
| S. sanguis | 3.5-7.03 | 3.6-7.25 | ND |
| S. oralis | >58 | >58 | ND |
| S. mitis | >58 | >58 | ND |

In general, G10 and G10CatC are more active against *E. coli, Pseudomonas,* and mutans *streptococci,* and less active against *Salmonella, Staphylococcus, Yersinia,* and the non-mutans streptococci. Of particular notice is that fusion of the targeting peptide to the N-terminus of G10 (G10CatC) enhanced killing activity 38-fold against Pak, but decreased killing activity 2-fold against *P. mendocina,* while the same fusion did not change the killing activity against *S. mutans.* In contrast, fusion of the targeting peptide to the C-terminus of G10 (G10CatN) significantly reduced killing activity against *E. coli,* but did not change killing activity against others. These results indicate that the position of the targeting peptide relative to the killing peptide plays an important role in determining the killing activity of the fusion peptide. Note that the targeting peptide CAT-1 alone does not have any antimicrobial activity.

c-3. Determination of Killing Kinetics

For non-specific antimicrobial peptide, the number of molecules bound to the cell surface is proportional to the peptide concentration in the solution, because binding is solely dependent on passive diffusion of the peptide through solution. However, if a targeting peptide is fused to the killing peptide, a higher concentration of peptide on the target cell surface could be achieved in a short period of time due to the high affinity, active binding of the targeting peptide to the target bacterial cells.

To show that increased killing activity of the fusion peptide is due to enhanced binding to the cell surface, time-kill assays were performed using a selected number of species, i.e. *P. aeruginosa,* and *P. mendocina.* Briefly, varying concentrations of peptide G10, G10CatC, or G10CatN was added to $10^5$ of target bacterial cells and survivors were counted by plating samples after 0.5, 1, 2 and 4 minutes of peptide exposure. Results are summarized in FIGS. 6-10.

Strikingly, at 9 μM concentration, the fusion peptide G10CatC achieved 2.5-log killing after 30 seconds, while treatment with G10 alone did not show significant killing until 4 minutes (1 $\log_{10}$ reduction). Concurrently, at 3 μM concentration, G10CatC treatment reduced the number of live *P. mendocina* cells to below detectable levels within 4 min, in contrast, G10 alone did not display any killing activity at the same concentration during the same time period. These data suggest that the addition of a targeting domain significantly improves the short-term killing rate against the target bacteria compared with the killing peptide alone. In contrast to G10C, G10CatN displayed no killing at any concentration tested through 4 minutes, suggesting that the G10 peptide must be fused to the C-terminus of the targeting domain to facilitate killing activity.

Of particular notice for *P. mendocina* is that although G10CatC has a 2× higher MBC than G10 alone, it kills much quicker in the kinetic analysis. This indicates that specific binding to the target cell surface allowed local accumulation of high concentration of the peptide in a short period of time (<4 minutes), thus enhanced killing kinetics.

The killing kinetics for PAK cells is similar (FIGS. 9 and 10). Here, G10 alone did not show any killing activity even at 18 μM concentration, in contrast, G10CatC killed >90% of PAK cells within 4 min at a lower concentration (9 μM).

Since G10 alone did not show significant killing activity within 4 min, another time-kill experiment was conducted with treatments lasting up to 2 h to get a more complete picture of killing kinetics. The results are summarized in FIG. 11. Similar to the short-term kinetic studies described above, treatment with 3 μM G10CatC killed all input *P. mendocina* cells within 30 min, in contrast, it took 2 h for G10 alone to kill all input *P. mendocina* cells at the same concentration. G10CatC also showed a more pronounced enhanced killing over G10 at 9 μM; no surviving *P. mendocina* cells were recovered after 2 minutes of treatment with G10CatC, but a significant number of cells were recovered even after 30 minutes of G10 exposure.

c-4. Determination of Killing Specificity

To test if G10CatC can selectively kill its target bacteria in a mixed culture, $10^5$ of *P. mendocina* and *E. coli* W3110 cells were mixed and treated with 6 µM G10 or G10CatC peptides. Samples were taken at 30 sec. 1 min, 2 min, and 4 min, and survivors were counted by plating assays. Preliminary results are summarized in FIGS. 12 and 13. It is apparent that treatment with G10CatC selectively reduced the number of *P. mendocina* cells from the mixed culture, and by 4 min no live *P. mendocina* cells could be detected. In contrast, the number of live W3110 cells remained nearly unchanged during the same period of treatment. As expected, treatment with G10 alone for 4 min did not affect the survival of *P. mendocina* nor W3110 cells.

To further demonstrate this effect, another mixed culture killing experiment was performed, in which PAK cells were mixed with *S. mutans* cells, and the cell mixture was treated with 9 µM G10CatC or G10 alone. As shown in FIGS. 14 and 15, G10 alone did not kill any of the cells within 4 min. In contrast, G10CatC killed over 90% of PAK cells, but none of *S. mutans* cells.

Taken together, these results demonstrate that G10CatC can specifically kill the bacterial species to which it specifically binds (the target cells), but not the non-target cells, although both types of cells are equally sensitive to the killing activity of the peptide (as demonstrated in MBC assay).

Although the invention has been described with reference to the presently preferred embodiment, it should be understood that various modifications can be made without departing from the spirit of the invention. Accordingly, the invention is limited only by the following claims.

What is claimed is:

1. A composition for killing microbial organisms, said composition comprising:
a targeting moiety comprising the amino acid sequence K-K-H-R-K-H-R-K-H-R-K-H (SEQ ID NO:61) attached to an antimicrobial peptide moiety, where said targeting moiety binds to a target microbial organism selected from the group consisting of *Pseudomonas* and *E. coli* and whereby said composition has an antimicrobial effect on said target microbial organism.

2. The composition of claim 1, wherein the targeting moiety is fused in-frame with the C terminus of said anti-microbial peptide moiety.

3. The composition of claim 1, wherein said antimicrobial peptide moiety is novispirin G10 comprising an amino acid sequence K-N-L-R-R-I-I-R-K-G-I-H-I-J-K-K-Y-G (SEQ ID NO:16).

4. The composition of claim 3, wherein the targeting moiety is fused in-frame with the C terminus of novispirin G10.

5. The composition of claims 1 or 3, wherein the targeting moiety and the anti-microbial peptide moiety are fused via a peptide linker to form a fusion peptide.

6. The composition of claim 5, wherein the fusion peptide comprises an amino acid sequence K-N-L-R-R-I-I-R-K-G-I-H-I-J-K-K-Y-G-G-G-S-G-G-S-K-K-H-R-K-H-R-K-H-R-K-H (SEQ ID NO: 71).

7. The composition of claim 5, wherein the peptide linker is from about 10 to 60 amino acids.

8. The composition of claim 7, wherein the peptide linker is from about 15 to 25 amino acids.

9. The composition of claim 8 wherein the peptide linker is about 15 amino acids.

10. The composition of claim 5, wherein the fusion peptide comprises an amino acid sequence K-K-H-R-K-H-R-K-H-R-K-H-G-G-S-G-G-S-K-N-L-R-R-I-I-R-K-G-I-H-I-I-K-K-Y-G (SEO ID NO:70).

11. The composition of claim 1, wherein the anti-microbial peptide moiety comprises a peptide selected from the group consisting of alexomycin, andropin, bacteriocin, β-pleated sheet bacteriocin, bactenecin, buforin, cathelicidin, α-helical clavanin, cecropin, dodecapeptide, defensin, β-defensin, α-defensin, gaegurin, histatin, indolicidin, magainin, nisin, protegrin, ranalexin, and tachyplesin.

12. The composition of claim 1, wherein the anti-microbial peptide moiety comprises a peptide selected from the group consisting of histatin 5, dhvarl, protegrin PG-1, and novispirin G10.

13. The composition of claim 1, wherein the target microbial organism is a member of the genus *Pseudomonas*.

14. The composition of claim 13, wherein the anti-microbial peptide moiety comprises a peptide selected from the group consisting of buforin, cecropin, indolicidin, and nisin.

15. The composition of claim 13, wherein the target microbial organism is *Pseudomonas aeruginosa*.

16. The composition of claim 15, wherein the anti-microbial peptide moiety comprises a peptide selected from the group consisting of magainin and renalexin.

17. The composition of claim 1, wherein the targeting moiety is fused in-frame with the anti-microbial peptide moiety through the N-terminus of the targeting moiety.

* * * * *

UNITED STATES PATENT AND TRADEMARK OFFICE
CERTIFICATE OF CORRECTION

PATENT NO. : 7,569,542 B2  Page 1 of 1
APPLICATION NO. : 10/706391
DATED : August 4, 2009
INVENTOR(S) : Randal Eckert et al.

It is certified that error appears in the above-identified patent and that said Letters Patent is hereby corrected as shown below:

Claim 3, Column 51, line 27:

"sequence K-N-L-R-R-I-I-R-K-G-I-H-I-J-K-K-Y-G (SEQ ID"

should read:

--sequence K-N-L-R-R-I-I-R-K-G-I-H-I-I-K-K-Y-G (SEQ ID--

Claim 6, Column 51, line 36:

"H-I-J-K-K-Y-G-G-G-S-G-G-S-K-K-H-R-K-H-R-K-H-R-"

should read:

--H-I-I-K-K-Y-G-G-G-S-G-G-S-K-K-H-R-K-H-R-K-H-R- --

Signed and Sealed this

Seventeenth Day of November, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,569,542 B2 | Page 1 of 1 |
| APPLICATION NO. | : 10/706391 | |
| DATED | : August 4, 2009 | |
| INVENTOR(S) | : Eckert et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 481 days.

Signed and Sealed this

Twenty-eighth Day of December, 2010

David J. Kappos
*Director of the United States Patent and Trademark Office*

SEQUENCE LISTING

```
<160> NUMBER OF SEQ ID NOS: 71

<210> SEQ ID NO 1
<211> LENGTH: 563
<212> TYPE: DNA
<213> ORGANISM: Artificial sequence
<220> FEATURE:
<223> OTHER INFORMATION: Synthesized using sequential PCR techniques

<400> SEQUENCE: 1
ggatatccac catggacttc gggttgagct tggttttcct tgtccttact ttaaaaggtg      60
tccagtgtga tagccacgct aagcggcacc acggatataa gcggaagttc cacgagaagc     120
accactcgca cagaggatac tctggtggcg gtggctcggg cggaggtggg tcgggtggcg     180
gcggatccga cgtgaagctt gtggagtctg ggggaggctt agtgaaccct ggagggtccc     240
tgaaactctc ctgtgcagcc tctggattca ctttcagtag ctataccatg tcttgggttc     300
gccagactcc ggagaagagg ctggagtggg tcgcatccat tagtagtggt ggtacttaca     360
cctactatcc agacagtgtg aagggccgat tcaccatctc cagagacaat gccaagaaca     420
ccctgtacct gcaaatgacc agtctgaagt ctgaggacac agccatgtat tactgttcaa     480
gagatgacgg ctcctacggc tcctattact atgctatgga ctactgggt caaggaacct     540 cagtcaccgt ctcttcagct agc                                             563

<210> SEQ ID NO 2
<211> LENGTH: 165
<212> TYPE: PRT
<213> ORGANISM: Artificial sequence
<220> FEATURE:
<223> OTHER INFORMATION: Synthesized using sequential PCR techniques

<400> SEQUENCE: 2

Asp Ser His Ala Lys Arg His His Gly Tyr Lys Arg Lys Phe His Glu
1               5                   10                  15

Lys His His Ser His Arg Gly Tyr Ser Gly Gly Gly Gly Ser Gly Gly
            20                  25                  30

Gly Gly Ser Gly Gly Gly Gly Ser Asp Val Lys Leu Val Glu Ser Gly
        35                  40                  45

Gly Gly Leu Val Asn Pro Gly Gly Ser Leu Lys Leu Ser Cys Ala Ala
    50                  55                  60

Ser Gly Phe Thr Phe Ser Ser Tyr Thr Met Ser Trp Val Arg Gln Thr
65                  70                  75                  80
```

```
Pro Glu Lys Arg Leu Glu Trp Val Ala Ser Ile Ser Ser Gly Gly Thr
                85                  90                  95

Tyr Thr Tyr Tyr Pro Asp Ser Val Lys Gly Arg Phe Thr Ile Ser Arg
            100                 105                 110

Asp Asn Ala Lys Asn Thr Leu Tyr Leu Gln Met Thr Ser Leu Lys Ser
        115                 120                 125

Glu Asp Thr Ala Met Tyr Tyr Cys Ser Arg Asp Gly Ser Tyr Gly
    130                 135                 140

Ser Tyr Tyr Tyr Ala Met Asp Tyr Trp Gly Gln Gly Thr Ser Val Thr
145                 150                 155                 160

Val Ser Ser Ala Ser
            165

<210> SEQ ID NO 3
<211> LENGTH: 533
<212> TYPE: DNA
<213> ORGANISM: Artificial sequence
<220> FEATURE:
<223> OTHER INFORMATION: Synthesized using sequential PCR techniques

<400> SEQUENCE: 3
ggatatccac catggacttc gggttgagct tggttttcct tgtccttact ttaaaaggtg    60
tccagtgtaa gcggctgttt aaggagctca agttcagcct gcgcaagtac tctggtggcg   120
gtggctcggg cggaggtggg tcgggtggcg gcggatccga cgtgaagctt gtggagtctg   180
ggggaggctt agtgaaccct ggagggtccc tgaaactctc ctgtgcagcc tctggattca   240 cttttcagtag ctataccatg tcttgggttc gccagactcc ggagaagagg ctggagtggg   300
tcgcatccat tagtagtggt ggtacttaca cctactatcc agacagtgtg aagggccgat   360
tcaccatctc cagagacaat gccaagaaca ccctgtacct gcaaatgacc agtctgaagt   420
ctgaggacac agccatgtat tactgttcaa gagatgacgg ctcctacggc tcctattact   480
atgctatgga ctactggggt caaggaacct cagtcaccgt ctcttcagct agc          533

<210> SEQ ID NO 4
<211> LENGTH: 155
<212> TYPE: PRT
<213> ORGANISM: Artificial sequence
<220> FEATURE:
<223> OTHER INFORMATION: Synthesized using sequential PCR techniques

<400> SEQUENCE: 4

Lys Arg Leu Phe Lys Glu Leu Lys Phe Ser Leu Arg Lys Tyr Ser Gly
1               5                   10                  15

Gly Gly Gly Ser Gly Gly Gly Gly Ser Gly Gly Gly Gly Ser Asp Val
            20                  25                  30

Lys Leu Val Glu Ser Gly Gly Gly Leu Val Asn Pro Gly Gly Ser Leu
        35                  40                  45

Lys Leu Ser Cys Ala Ala Ser Gly Phe Thr Phe Ser Ser Tyr Thr Met
    50                  55                  60

Ser Trp Val Arg Gln Thr Pro Glu Lys Arg Leu Glu Trp Val Ala Ser
65                  70                  75                  80

Ile Ser Ser Gly Gly Thr Tyr Thr Tyr Tyr Pro Asp Ser Val Lys Gly
                85                  90                  95

Arg Phe Thr Ile Ser Arg Asp Asn Ala Lys Asn Thr Leu Tyr Leu Gln
            100                 105                 110

Met Thr Ser Leu Lys Ser Glu Asp Thr Ala Met Tyr Tyr Cys Ser Arg
```

```
            115                 120                 125
Asp Asp Gly Ser Tyr Gly Ser Tyr Tyr Tyr Ala Met Asp Tyr Trp Gly
    130                 135                 140

Gln Gly Thr Ser Val Thr Val Ser Ser Ala Ser
145                 150                 155

<210> SEQ ID NO 5
<211> LENGTH: 24
<212> TYPE: PRT
<213> ORGANISM: Artificial sequence
<220> FEATURE:
<223> OTHER INFORMATION: Synthesized using sequential PCR techniques

<400> SEQUENCE: 5

Asp Ser His Ala Lys Arg His His Gly Tyr Lys Arg Lys Phe His Glu
1               5                   10                  15

Lys His His Ser His Arg Gly Tyr
            20

<210> SEQ ID NO 6
<211> LENGTH: 14
<212> TYPE: PRT
<213> ORGANISM: Artificial sequence
<220> FEATURE:
<223> OTHER INFORMATION: Synthesized using sequential PCR techniques

<400> SEQUENCE: 6

Lys Arg Leu Phe Lys Glu Leu Lys Phe Ser Leu Arg Lys Tyr
1               5                   10

<210> SEQ ID NO 7
<211> LENGTH: 89
<212> TYPE: DNA
<213> ORGANISM: Artificial sequence
<220> FEATURE:
<223> OTHER INFORMATION: Primer 986

<400> SEQUENCE: 7
caccactcgc acagaggata ctctggtggc ggtggctcgg gcggaggtgg gtcgggtggc      60
ggcggatccg acgtgaagct tgtggagtc                                       89

<210> SEQ ID NO 8
<211> LENGTH: 84
<212> TYPE: DNA
<213> ORGANISM: Artificial sequence
<220> FEATURE:
<223> OTHER INFORMATION: Primer 987

<400> SEQUENCE: 8
ggtgtccagt gtgatagcca cgctaagcgg caccacggat ataagcggaa gttccacgag      60
aagcaccact cgcacagagg atac                                            84

<210> SEQ ID NO 9
<211> LENGTH: 74
<212> TYPE: DNA
<213> ORGANISM: Artificial sequence
<220> FEATURE:
<223> OTHER INFORMATION: Primer 988

<400> SEQUENCE: 9
gatatccacc atggacttcg ggttgagctt ggttttcctt gtccttactt taaaaggtgt      60
ccagtgtgat agcc                                                       74
```

```
<210> SEQ ID NO 10
<211> LENGTH: 87
<212> TYPE: DNA
<213> ORGANISM: Artificial sequence
<220> FEATURE:
<223> OTHER INFORMATION: Primer 989

<400> SEQUENCE: 10
gttcagcctg cgcaagtact ctggtggcgg tggctcgggc ggaggtgggt cgggtggcgg      60
cggatccgac gtgaagcttg tggagtc                                         87

<210> SEQ ID NO 11
<211> LENGTH: 69
<212> TYPE: DNA
<213> ORGANISM: Artificial sequence
<220> FEATURE:
<223> OTHER INFORMATION: Primer 990

<400> SEQUENCE: 11
gtccttactt taaaaggtgt ccagtgtaag cggctgttta aggagctcaa gttcagcctg      60
cgcaagtac                                                             69

<210> SEQ ID NO 12
<211> LENGTH: 65
<212> TYPE: DNA
<213> ORGANISM: Artificial sequence
<220> FEATURE:
<223> OTHER INFORMATION: Primer 991

<400> SEQUENCE: 12
ggatatccac catggacttc gggttgagct tggttttcct tgtccttact ttaaaaggtg      60
tccag                                                                 65

<210> SEQ ID NO 13
<211> LENGTH: 39
<212> TYPE: DNA
<213> ORGANISM: Artificial sequence
<220> FEATURE:
<223> OTHER INFORMATION: Primer 452

<400> SEQUENCE: 13
tgggtcgacw gatggggstg ttgtgctagc tgaggagac                             39

<210> SEQ ID NO 14
<211> LENGTH: 12
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa is Val, Gln or His
<220> FEATURE:
<221> NAME/KEY: MISC_FEATURE
<222> LOCATION: (2)..(2)
<223> OTHER INFORMATION: Xaa is Pro or His
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (6)..(6)
<223> OTHER INFORMATION: Xaa is Lys or His
<220> FEATURE:
<221> NAME/KEY: MISC_FEATURE
```

```
<222> LOCATION: (7)..(7)
<223> OTHER INFORMATION: Xaa is His or Ala
<220> FEATURE:
<221> NAME/KEY: MISC_FEATURE
<222> LOCATION: (8)..(8)
<223> OTHER INFORMATION: Xaa is Leu or His
<220> FEATURE:
<221> NAME/KEY: MISC_FEATURE
<222> LOCATION: (9)..(9)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is Lys or Arg
<220> FEATURE:
<221> NAME/KEY: MISC_FEATURE
<222> LOCATION: (12)..(12)
<223> OTHER INFORMATION: Xaa is Pro or Leu

<400> SEQUENCE: 14

Xaa Xaa His Glu Xaa Xaa Xaa Xaa Xaa Xaa Xaa Xaa
1               5                   10

<210> SEQ ID NO 15
<211> LENGTH: 18
<212> TYPE: PRT
<213> ORGANISM: Artificial sequence
<220> FEATURE:
<223> OTHER INFORMATION: Protegrin PG-1

<400> SEQUENCE: 15

Arg Gly Gly Arg Leu Cys Tyr Cys Arg Arg Arg Phe Cys Val Cys Val
1               5                   10                  15

Gly Arg

<210> SEQ ID NO 16
<211> LENGTH: 18
<212> TYPE: PRT
<213> ORGANISM: Artificial sequence
<220> FEATURE:
<223> OTHER INFORMATION: Novispirin G10

<400> SEQUENCE: 16

Lys Asn Leu Arg Arg Ile Ile Arg Lys Gly Ile His Ile Ile Lys Lys
1               5                   10                  15

Tyr Gly

<210> SEQ ID NO 17
<211> LENGTH: 15
<212> TYPE: PRT
<213> ORGANISM: Artificial sequence
<220> FEATURE:
<223> OTHER INFORMATION: Linker peptide

<400> SEQUENCE: 17

Ser Gly Gly Gly Gly Ser Gly Gly Gly Ser Gly Gly Gly Gly
1               5                   10                  15

<210> SEQ ID NO 18
<211> LENGTH: 8
<212> TYPE: PRT
<213> ORGANISM: Artificial sequence
<220> FEATURE:
<223> OTHER INFORMATION: Linker peptide
```

<400> SEQUENCE: 18

Gly Gly Gly Ser Gly Gly Gly Ser
1               5

<210> SEQ ID NO 19
<211> LENGTH: 57
<212> TYPE: DNA
<213> ORGANISM: Artificial sequence
<220> FEATURE:
<223> OTHER INFORMATION: Anti-microbial peptide

<400> SEQUENCE: 19
cgtggcggtc gcctatgcta ctgtcgacgt cgcttttgcg tatgcgtggg acggtct      57

<210> SEQ ID NO 20
<211> LENGTH: 29
<212> TYPE: DNA
<213> ORGANISM: Artificial sequence
<220> FEATURE:
<223> OTHER INFORMATION: Amplification primer

<400> SEQUENCE: 20
gggaattccg tggcggtcgc ctatgctac                                     29

<210> SEQ ID NO 21
<211> LENGTH: 44
<212> TYPE: DNA
<213> ORGANISM: Artificial sequence
<220> FEATURE:
<223> OTHER INFORMATION: Amplification primer

<400> SEQUENCE: 21
agagccgcca cccgaacctc cgcctgaaga gacggtgact gagg                    44

<210> SEQ ID NO 22
<211> LENGTH: 39
<212> TYPE: DNA
<213> ORGANISM: Artificial sequence
<220> FEATURE:
<223> OTHER INFORMATION: Amplification primer

<400> SEQUENCE: 22
ggttcgggtg gcggctctga tgttgtgatg acccagact                          39

<210> SEQ ID NO 23
<211> LENGTH: 47
<212> TYPE: DNA
<213> ORGANISM: Artificial sequence
<220> FEATURE:
<223> OTHER INFORMATION: Amplification primer

<400> SEQUENCE: 23
ggtctagatt cccagaaccc ccaccccttac gtttcagctc cagcttg                47

<210> SEQ ID NO 24
<211> LENGTH: 12
<212> TYPE: PRT
<213> ORGANISM: Artificial sequence
<220> FEATURE:
<223> OTHER INFORMATION: Peptide library

<400> SEQUENCE: 24

Val Pro His Glu Phe Lys His Leu Gln Met Lys Pro
1               5                   10

<210> SEQ ID NO 25
<211> LENGTH: 12
<212> TYPE: PRT
<213> ORGANISM: Artificial sequence
<220> FEATURE:
<223> OTHER INFORMATION: Peptide library

<400> SEQUENCE: 25

Val Pro His Glu Phe Lys His Leu Gln Met Lys Pro
1               5                   10

<210> SEQ ID NO 26
<211> LENGTH: 12
<212> TYPE: PRT
<213> ORGANISM: Artificial sequence
<220> FEATURE:
<223> OTHER INFORMATION: Peptide library

<400> SEQUENCE: 26

His His His Lys Ala Leu Ala Pro Thr Val Thr Gly
1               5                   10

<210> SEQ ID NO 27
<211> LENGTH: 12
<212> TYPE: PRT
<213> ORGANISM: Artificial sequence
<220> FEATURE:
<223> OTHER INFORMATION: Peptide library

<400> SEQUENCE: 27

Val Pro His Glu Phe His Ala His Arg Gly Arg Leu
1               5                   10

<210> SEQ ID NO 28
<211> LENGTH: 12
<212> TYPE: PRT
<213> ORGANISM: Artificial sequence
<220> FEATURE:
<223> OTHER INFORMATION: Peptide library

<400> SEQUENCE: 28

Val Pro His Glu Phe Lys His Leu Gln Met Lys Pro
1               5                   10

<210> SEQ ID NO 29
<211> LENGTH: 12
<212> TYPE: PRT
<213> ORGANISM: Artificial sequence
<220> FEATURE:
<223> OTHER INFORMATION: Peptide library

<400> SEQUENCE: 29

Gln Pro His Pro His Lys Val His Ser Leu Pro Pro
1               5                   10

<210> SEQ ID NO 30
<211> LENGTH: 12
<212> TYPE: PRT
<213> ORGANISM: Artificial sequence
<220> FEATURE:
<223> OTHER INFORMATION: Peptide library

<400> SEQUENCE: 30

Val Pro His Glu Phe His Ala His Arg Gly Arg Leu
1               5                   10

<210> SEQ ID NO 31

```
<210> SEQ ID NO 31
<211> LENGTH: 12
<212> TYPE: PRT
<213> ORGANISM: Artificial sequence
<220> FEATURE:
<223> OTHER INFORMATION: Peptide library

<400> SEQUENCE: 31

Val Pro His Glu Phe His Ala His Arg Gly Arg Leu
1               5                   10

<210> SEQ ID NO 32
<211> LENGTH: 12
<212> TYPE: PRT
<213> ORGANISM: Artificial sequence
<220> FEATURE:
<223> OTHER INFORMATION: Peptide library

<400> SEQUENCE: 32

His His Leu His Tyr Asn Pro Ala Phe Pro Gly Leu
1               5                   10

<210> SEQ ID NO 33
<211> LENGTH: 12
<212> TYPE: PRT
<213> ORGANISM: Artificial sequence
<220> FEATURE:
<223> OTHER INFORMATION: Peptide library

<400> SEQUENCE: 33

Gln Pro Ala Pro Tyr Ile Ser Ser Pro Ser Ala Ser
1               5                   10

<210> SEQ ID NO 34
<211> LENGTH: 12
<212> TYPE: PRT
<213> ORGANISM: Artificial sequence
<220> FEATURE:
<223> OTHER INFORMATION: Peptide library

<400> SEQUENCE: 34

Val Arg Leu Pro Leu Trp Leu Pro Ser Leu Asn Glu
1               5                   10

<210> SEQ ID NO 35
<211> LENGTH: 12
<212> TYPE: PRT
<213> ORGANISM: Artificial sequence
<220> FEATURE:
<223> OTHER INFORMATION: Peptide library

<400> SEQUENCE: 35

Ala Asn Tyr Phe Leu Pro Pro Val Leu Ser Ser Ser
1               5                   10

<210> SEQ ID NO 36
<211> LENGTH: 12
<212> TYPE: PRT
<213> ORGANISM: Artificial sequence
<220> FEATURE:
<223> OTHER INFORMATION: Peptide library

<400> SEQUENCE: 36

Ser His Pro Trp Asn Ala Gln Arg Glu Leu Ser Val
1               5                   10

<210> SEQ ID NO 37
<211> LENGTH: 12
```

```
<212> TYPE: PRT
<213> ORGANISM: Artificial sequence
<220> FEATURE:
<223> OTHER INFORMATION: Peptide library

<400> SEQUENCE: 37

Ser Val Ser Val Gly Met Arg Pro Met Pro Arg Pro
1               5                   10

<210> SEQ ID NO 38
<211> LENGTH: 12
<212> TYPE: PRT
<213> ORGANISM: Artificial sequence
<220> FEATURE:
<223> OTHER INFORMATION: Peptide library

<400> SEQUENCE: 38

Trp Thr Pro Leu His Pro Ser Thr Asn Arg Pro Pro
1               5                   10

<210> SEQ ID NO 39
<211> LENGTH: 12
<212> TYPE: PRT
<213> ORGANISM: Artificial sequence
<220> FEATURE:
<223> OTHER INFORMATION: Peptide library

<400> SEQUENCE: 39

Ser Val Ser Val Gly Met Lys Pro Ser Pro Arg Pro
1               5                   10

<210> SEQ ID NO 40
<211> LENGTH: 12
<212> TYPE: PRT
<213> ORGANISM: Artificial sequence
<220> FEATURE:
<223> OTHER INFORMATION: Peptide library

<400> SEQUENCE: 40

Ser Val Ser Val Gly Met Lys Pro Ser Pro Arg Pro
1               5                   10

<210> SEQ ID NO 41
<211> LENGTH: 12
<212> TYPE: PRT
<213> ORGANISM: Artificial sequence
<220> FEATURE:
<223> OTHER INFORMATION: Peptide library

<400> SEQUENCE: 41

Ser Val Pro Val Gly Pro Tyr Asn Glu Ser Gln Pro
1               5                   10

<210> SEQ ID NO 42
<211> LENGTH: 12
<212> TYPE: PRT
<213> ORGANISM: Artificial sequence
<220> FEATURE:
<223> OTHER INFORMATION: Peptide library

<400> SEQUENCE: 42

Trp Ala Pro Pro Leu Phe Arg Ser Ser Leu Phe Tyr
1               5                   10

<210> SEQ ID NO 43
<211> LENGTH: 12
<212> TYPE: PRT
```

```
<213> ORGANISM: Artificial sequence
<220> FEATURE:
<223> OTHER INFORMATION: Peptide library
<220> FEATURE:
<221> NAME/KEY: MISC_FEATURE
<222> LOCATION: (1)..(12)
<223> OTHER INFORMATION: Xaa is any amino acid

<400> SEQUENCE: 43

Trp Ala Pro Pro Xaa Pro Xaa Ser Ser Leu Phe Tyr
1               5                   10

<210> SEQ ID NO 44
<211> LENGTH: 12
<212> TYPE: PRT
<213> ORGANISM: Artificial sequence
<220> FEATURE:
<223> OTHER INFORMATION: Peptide library

<400> SEQUENCE: 44

His His Gly Trp Thr His His Trp Pro Pro Pro Pro
1               5                   10

<210> SEQ ID NO 45
<211> LENGTH: 12
<212> TYPE: PRT
<213> ORGANISM: Artificial sequence
<220> FEATURE:
<223> OTHER INFORMATION: Peptide library

<400> SEQUENCE: 45

Ser Tyr Tyr Ser Leu Pro Pro Ile Phe His Ile Pro
1               5                   10

<210> SEQ ID NO 46
<211> LENGTH: 13
<212> TYPE: PRT
<213> ORGANISM: Artificial sequence
<220> FEATURE:
<223> OTHER INFORMATION: Peptide library

<400> SEQUENCE: 46

His Phe Gln Glu Asn Pro Leu Ser Arg Gly Gly Glu Leu
1               5                   10

<210> SEQ ID NO 47
<211> LENGTH: 12
<212> TYPE: PRT
<213> ORGANISM: Artificial sequence
<220> FEATURE:
<223> OTHER INFORMATION: Peptide library

<400> SEQUENCE: 47

Phe Ser Tyr Ser Pro Thr Arg Ala Pro Leu Asn Met
1               5                   10

<210> SEQ ID NO 48
<211> LENGTH: 12
<212> TYPE: PRT
<213> ORGANISM: Artificial sequence
<220> FEATURE:
<223> OTHER INFORMATION: Peptide library
<220> FEATURE:
<221> NAME/KEY: MISC_FEATURE
<222> LOCATION: (1)..(12)
<223> OTHER INFORMATION: Xaa is any amino acid

<400> SEQUENCE: 48
```

```
Ser Xaa Pro Xaa Xaa Met Lys Xaa Ser Xaa Xaa Xaa
1               5                   10

<210> SEQ ID NO 49
<211> LENGTH: 12
<212> TYPE: PRT
<213> ORGANISM: Artificial sequence
<220> FEATURE:
<223> OTHER INFORMATION: Peptide library

<400> SEQUENCE: 49

Val Ser Arg His Gln Ser Trp His Pro His Asp Leu
1               5                   10

<210> SEQ ID NO 50
<211> LENGTH: 12
<212> TYPE: PRT
<213> ORGANISM: Artificial sequence
<220> FEATURE:
<223> OTHER INFORMATION: Peptide library
<220> FEATURE:
<221> NAME/KEY: MISC_FEATURE
<222> LOCATION: (1)..(12)
<223> OTHER INFORMATION: Xaa is any amino acid

<400> SEQUENCE: 50

Asp Tyr Xaa Tyr Arg Gly Leu Pro Arg Xaa Glu Thr
1               5                   10

<210> SEQ ID NO 51
<211> LENGTH: 12
<212> TYPE: PRT
<213> ORGANISM: Artificial sequence
<220> FEATURE:
<223> OTHER INFORMATION: Peptide library

<400> SEQUENCE: 51

Ser Val Ser Val Gly Met Lys Pro Ser Pro Arg Pro
1               5                   10

<210> SEQ ID NO 52
<211> LENGTH: 12
<212> TYPE: PRT
<213> ORGANISM: Artificial sequence
<220> FEATURE:
<223> OTHER INFORMATION: Peptide library

<400> SEQUENCE: 52

Lys His Leu Gln Asn Arg Ser Thr Gly Tyr Glu Thr
1               5                   10

<210> SEQ ID NO 53
<211> LENGTH: 12
<212> TYPE: PRT
<213> ORGANISM: Artificial sequence
<220> FEATURE:
<223> OTHER INFORMATION: Peptide library

<400> SEQUENCE: 53

His Ile His Ser Leu Ser Pro Ser Lys Thr Trp Pro
1               5                   10

<210> SEQ ID NO 54
<211> LENGTH: 12
<212> TYPE: PRT
<213> ORGANISM: Artificial sequence
<220> FEATURE:
<223> OTHER INFORMATION: Peptide library
```

```
<400> SEQUENCE: 54

Thr Ile Thr Pro Thr Asp Ala Glu Met Pro Phe Leu
1               5                   10

<210> SEQ ID NO 55
<211> LENGTH: 12
<212> TYPE: PRT
<213> ORGANISM: Artificial sequence
<220> FEATURE:
<223> OTHER INFORMATION: Peptide library

<400> SEQUENCE: 55

His Leu Leu Glu Ser Gly Val Leu Glu Arg Gly Met
1               5                   10

<210> SEQ ID NO 56
<211> LENGTH: 12
<212> TYPE: PRT
<213> ORGANISM: Artificial sequence
<220> FEATURE:
<223> OTHER INFORMATION: Peptide library

<400> SEQUENCE: 56

His Asp Arg Tyr His Ile Pro Pro Leu Gln Leu His
1               5                   10

<210> SEQ ID NO 57
<211> LENGTH: 12
<212> TYPE: PRT
<213> ORGANISM: Artificial sequence
<220> FEATURE:
<223> OTHER INFORMATION: Peptide library

<400> SEQUENCE: 57

Val Asn Thr Leu Gln Asn Val Arg His Met Ala Ala
1               5                   10

<210> SEQ ID NO 58
<211> LENGTH: 12
<212> TYPE: PRT
<213> ORGANISM: Artificial sequence
<220> FEATURE:
<223> OTHER INFORMATION: Peptide library

<400> SEQUENCE: 58

Ser Asn Tyr Met Lys Leu Arg Ala Val Ser Pro Phe
1               5                   10

<210> SEQ ID NO 59
<211> LENGTH: 12
<212> TYPE: PRT
<213> ORGANISM: Artificial sequence
<220> FEATURE:
<223> OTHER INFORMATION: Peptide library

<400> SEQUENCE: 59

Asn Leu Gln Met Pro Tyr Ala Trp Arg Thr Glu Phe
1               5                   10

<210> SEQ ID NO 60
<211> LENGTH: 12
<212> TYPE: PRT
<213> ORGANISM: Artificial sequence
<220> FEATURE:
<223> OTHER INFORMATION: Peptide library
```

<400> SEQUENCE: 60

Gln Lys Pro Leu Thr Gly Pro His Phe Ser Leu Ile
1               5                   10

<210> SEQ ID NO 61
<211> LENGTH: 12
<212> TYPE: PRT
<213> ORGANISM: Artificial sequence
<220> FEATURE:
<223> OTHER INFORMATION: Design peptide

<400> SEQUENCE: 61

Lys Lys His Arg Lys His Arg Lys His Arg Lys His
1               5                   10

<210> SEQ ID NO 62
<211> LENGTH: 16
<212> TYPE: PRT
<213> ORGANISM: Artificial sequence
<220> FEATURE:
<223> OTHER INFORMATION: Design peptide

<400> SEQUENCE: 62

Arg Gly Leu Arg Arg Leu Gly Arg Arg Gly Leu Arg Arg Leu Gly Arg
1               5                   10                  15

<210> SEQ ID NO 63
<211> LENGTH: 13
<212> TYPE: PRT
<213> ORGANISM: Artificial sequence
<220> FEATURE:
<223> OTHER INFORMATION: Design peptide

<400> SEQUENCE: 63

Lys Pro Val Leu Pro Val Leu Pro Val Leu Pro Val Leu
1               5                   10

<210> SEQ ID NO 64
<211> LENGTH: 16
<212> TYPE: PRT
<213> ORGANISM: Artificial sequence
<220> FEATURE:
<223> OTHER INFORMATION: Design peptide

<400> SEQUENCE: 64

Val Leu Arg Ile Ile Arg Ile Ala Val Leu Arg Ile Ile Arg Ile Ala
1               5                   10                  15

<210> SEQ ID NO 65
<211> LENGTH: 15
<212> TYPE: PRT
<213> ORGANISM: Artificial sequence
<220> FEATURE:
<223> OTHER INFORMATION: Design peptide

<400> SEQUENCE: 65

Leu Pro Glu Thr Gly Gly Ser Gly Gly Ser Leu Pro Glu Thr Gly
1               5                   10                  15

<210> SEQ ID NO 66
<211> LENGTH: 11
<212> TYPE: PRT
<213> ORGANISM: Artificial sequence
<220> FEATURE:
<223> OTHER INFORMATION: Design peptide

<400> SEQUENCE: 66

```
Arg Ala His Ile Arg Arg Ala His Ile Arg Arg
1               5                   10

<210> SEQ ID NO 67
<211> LENGTH: 14
<212> TYPE: PRT
<213> ORGANISM: Artificial sequence
<220> FEATURE:
<223> OTHER INFORMATION: Design peptide

<400> SEQUENCE: 67

Asp Glu Asp Glu Asp Asp Glu Glu Asp Asp Asp Glu Glu Glu
1               5                   10

<210> SEQ ID NO 68
<211> LENGTH: 15
<212> TYPE: PRT
<213> ORGANISM: Artificial sequence
<220> FEATURE:
<223> OTHER INFORMATION: Design peptide

<400> SEQUENCE: 68

Ser Thr Met Cys Gly Ser Thr Met Cys Gly Ser Thr Met Cys Gly
1               5                   10                  15

<210> SEQ ID NO 69
<211> LENGTH: 5
<212> TYPE: PRT
<213> ORGANISM: Artificial sequence
<220> FEATURE:
<223> OTHER INFORMATION: Linker peptide

<400> SEQUENCE: 69

Gly Gly Ser Gly Gly
1               5

<210> SEQ ID NO 70
<211> LENGTH: 36
<212> TYPE: PRT
<213> ORGANISM: Artificial sequence
<220> FEATURE:
<223> OTHER INFORMATION: Fusion peptide

<400> SEQUENCE: 70

Lys Lys His Arg Lys His Arg Lys His Arg Lys His Gly Gly Ser Gly
1               5                   10                  15

Gly Ser Lys Asn Leu Arg Arg Ile Ile Arg Lys Gly Ile His Ile Ile
            20                  25                  30

Lys Lys Tyr Gly
        35

<210> SEQ ID NO 71
<211> LENGTH: 36
<212> TYPE: PRT
<213> ORGANISM: Artificial sequence
<220> FEATURE:
<223> OTHER INFORMATION: Fusion peptide

<400> SEQUENCE: 71

Lys Asn Leu Arg Arg Ile Ile Arg Lys Gly Ile His Ile Ile Lys Lys
1               5                   10                  15
```

```
Tyr Gly Gly Gly Ser Gly Gly Ser Lys Lys His Arg Lys His Arg Lys
             20                  25                  30
His Arg Lys His
         35
```